(12) United States Patent
Huang et al.

(10) Patent No.: US 11,891,670 B2
(45) Date of Patent: Feb. 6, 2024

(54) PROBES, MICROARRAY, PRIMERS, KIT AND APPLICATIONS FOR RAPID DETECTION OF CLINICAL OPHTHALMIC MICROORGANISMS

(71) Applicant: Affiliated Eye Institute of Shandong First Medical University, Qingdao (CN)

(72) Inventors: Yusen Huang, Qingdao (CN); Bining Zhang, Qingdao (CN); Wenfeng Li, Qingdao (CN); Qing Liu, Qingdao (CN); Zhichao Ren, Qingdao (CN); Huabo Chen, Qingdao (CN)

(73) Assignee: AFFILIATED EYE INSTITUTE OF SHANDONG FIRST MEDICAL UNIVERSITY, Qingdao (CN)

( * ) Notice: Subject to any disclaimer, the term of this patent is extended or adjusted under 35 U.S.C. 154(b) by 0 days.

(21) Appl. No.: 17/929,875

(22) Filed: Sep. 6, 2022

(65) Prior Publication Data
US 2023/0008908 A1    Jan. 12, 2023

Related U.S. Application Data

(63) Continuation of application No. PCT/CN2021/137383, filed on Dec. 13, 2021.

(30) Foreign Application Priority Data

Dec. 30, 2020    (CN) .......................... 202011604557.8

(51) Int. Cl.
| | | |
|---|---|---|
| C12Q 1/689 | (2018.01) | |
| C12Q 1/6816 | (2018.01) | |
| C12Q 1/6837 | (2018.01) | |
| C12Q 1/6844 | (2018.01) | |
| C07H 21/00 | (2006.01) | |

(52) U.S. Cl.
CPC ........... *C12Q 1/689* (2013.01); *C12Q 1/6816* (2013.01); *C12Q 1/6837* (2013.01); *C12Q 1/6844* (2013.01)

(58) Field of Classification Search
CPC .................................. C12Q 1/68; C07H 21/00
See application file for complete search history.

(56) References Cited

U.S. PATENT DOCUMENTS

2001/0053519 A1* 12/2001 Fodor .................... B82Y 30/00
536/24.1
2002/0151078 A1* 10/2002 Kellogg ................ B01L 3/5027
436/180
2004/0072242 A1    4/2004 Hunter et al.

FOREIGN PATENT DOCUMENTS

| CN | 1414112 A | 4/2003 |
| CN | 102080127 A | 6/2011 |
| CN | 105331610 A | 2/2016 |
| CN | 105969854 A | 9/2016 |

OTHER PUBLICATIONS

Fernandez-No et al., Food Microbiology 28: 605 (Year: 2011).*
Rotolo et al., BioControl 61 : 91 (Year: 2016).*
Stratagene Catalog. 39 (Year: 1988).*
Xie et al., J. of Applied Microbiology 128 : 518 (Year: 2019).*
Huaqing Gong, Ye Wang, Xia Qi, Chunxia Wang, Ting Liu, Shengwei Ren, Yiqiang Wang, "Differential response of lens crystallins and corneal crystallins in degenerative corneas", Experimental Eye Research, 2012, pp. 55-64, vol. 96.
Zhang Yinglang, Wang Liya, Li Zhitao, Sun Shengtao, "Application of gene chip technique in identification of pathogens spaces in fungal keratitis", Clin Ophthal Res, May 2007, pp. 379-382, vol. 25, No. 5.
Tong Mei-qin, Shang Shi-qiang , Wu Yi-dong , Zhao Zhen-yan, "Rapid diagosis of neonatal sepsis by 16SrRNA genes PCR amplification and genechip hybridization", Clin J Pediatr, Septmber 2004, pp. 663-667, vol. 42, No. 9.
Rajagopalaboopathi Jayasudha, Venkatapathy Narendran, Palanisamy Manikandan, Solai Ramatchandirane Prabagaran, "Identification of Polybacterial Communities in Patients with Postoperative, Posttraumatic, and Endogenous Endophthalmitis through 16S rRNA Gene Libraries", Journal of Clinical Microbiology, May 2014, pp. 1459-1466, vol. 52, No. 5.

* cited by examiner

*Primary Examiner* — Ethan C Whisenant
(74) *Attorney, Agent, or Firm* — Rachel Pilloff; Sean Passino; Martin Cosenza

(57) ABSTRACT

Disclosed are probes, primers, a microarray, a kit and applications for rapid detection of clinical microorganism in ophthalmology, belonging to that technical field of clinical microorganism detection. The probes of that disclosure comprise probes for respectively detect *Staphylococcus epidermidis, Staphylococcus aureus, Staphylococcus haemolyticus, Pseudomonas aeruginosa, Staphylococcus hominis, Serratia marcescens, Escherichia coli, Bacillus subtilis* and *Enterobacter cloacae*. The disclosure also discloses primers for amplifying the target bacteria, which comprises primers which can amplify gene sequence fragments with intraspecies homology of more than 95 percent (%) and interspecies homology of less than 75%. The disclosure also provides a method for synthesizing the hybridization probe on the microarray, a method for hybridization reaction and a method for scanning detection. The probes described in the present invention are highly specific and detects microorganisms in ophthalmic clinical samples with sufficient positivity, high accuracy and deliver diagnosis in a short period of time.

2 Claims, 10 Drawing Sheets

Specification includes a Sequence Listing.

SEQUENCE LISTING

```
Sequence total quantity: 174
SEQ ID NO: 1                moltype = DNA  length = 25
FEATURE                     Location/Qualifiers
source                      1..25
                            mol_type = other DNA
                            organism = synthetic construct
SEQUENCE: 1
atcaaacgac taatacaatt actgg                                                 25

SEQ ID NO: 2                moltype = DNA  length = 25
FEATURE                     Location/Qualifiers
source                      1..25
                            mol_type = other DNA
                            organism = synthetic construct
SEQUENCE: 2
actaatacaa ttactggcac gccaa                                                 25

SEQ ID NO: 3                moltype = DNA  length = 25
FEATURE                     Location/Qualifiers
source                      1..25
                            mol_type = other DNA
                            organism = synthetic construct
SEQUENCE: 3
aattactggc acgccaagtg aagta                                                 25

SEQ ID NO: 4                moltype = DNA  length = 25
FEATURE                     Location/Qualifiers
source                      1..25
                            mol_type = other DNA
                            organism = synthetic construct
SEQUENCE: 4
gcacgccaag tgaagtagga actac                                                 25

SEQ ID NO: 5                moltype = DNA  length = 25
FEATURE                     Location/Qualifiers
source                      1..25
                            mol_type = other DNA
                            organism = synthetic construct
SEQUENCE: 5
agtgaagtag gaactacaac tgtga                                                 25

SEQ ID NO: 6                moltype = DNA  length = 25
FEATURE                     Location/Qualifiers
source                      1..25
                            mol_type = other DNA
                            organism = synthetic construct
SEQUENCE: 6
aggaactaca actgtgacag ttaat                                                 25

SEQ ID NO: 7                moltype = DNA  length = 25
FEATURE                     Location/Qualifiers
source                      1..25
                            mol_type = other DNA
                            organism = synthetic construct
SEQUENCE: 7
caactgtgac agttaatacg actga                                                 25

SEQ ID NO: 8                moltype = DNA  length = 25
FEATURE                     Location/Qualifiers
source                      1..25
                            mol_type = other DNA
                            organism = synthetic construct
SEQUENCE: 8
acagttaata cgactgatgc tactg                                                 25

SEQ ID NO: 9                moltype = DNA  length = 25
FEATURE                     Location/Qualifiers
source                      1..25
                            mol_type = other DNA
                            organism = synthetic construct
SEQUENCE: 9
tacgactgat gctactggga acgta                                                 25

SEQ ID NO: 10               moltype = DNA  length = 25
FEATURE                     Location/Qualifiers
source                      1..25
                            mol_type = other DNA
                            organism = synthetic construct
```

```
SEQUENCE: 10
atgctactgg gaacgtaaca tctaa                                              25

SEQ ID NO: 11          moltype = DNA   length = 25
FEATURE                Location/Qualifiers
source                 1..25
                       mol_type = other DNA
                       organism = synthetic construct
SEQUENCE: 11
gggaacgtaa catctaagca attta                                              25

SEQ ID NO: 12          moltype = DNA   length = 25
FEATURE                Location/Qualifiers
source                 1..25
                       mol_type = other DNA
                       organism = synthetic construct
SEQUENCE: 12
aacatctaag caatttacaa taacg                                              25

SEQ ID NO: 13          moltype = DNA   length = 25
FEATURE                Location/Qualifiers
source                 1..25
                       mol_type = other DNA
                       organism = synthetic construct
SEQUENCE: 13
atacaatcag ccctgttgta aatgt                                              25

SEQ ID NO: 14          moltype = DNA   length = 25
FEATURE                Location/Qualifiers
source                 1..25
                       mol_type = other DNA
                       organism = synthetic construct
SEQUENCE: 14
agccctgttg taaatgtgac gccaa                                              25

SEQ ID NO: 15          moltype = DNA   length = 25
FEATURE                Location/Qualifiers
source                 1..25
                       mol_type = other DNA
                       organism = synthetic construct
SEQUENCE: 15
tgtaaatgtg acgccaagtc aagca                                              25

SEQ ID NO: 16          moltype = DNA   length = 25
FEATURE                Location/Qualifiers
source                 1..25
                       mol_type = other DNA
                       organism = synthetic construct
SEQUENCE: 16
tgacgccaag tcaagcatca gaagt                                              25

SEQ ID NO: 17          moltype = DNA   length = 25
FEATURE                Location/Qualifiers
source                 1..25
                       mol_type = other DNA
                       organism = synthetic construct
SEQUENCE: 17
agtcaagcat cagaagtttt cacgc                                              25

SEQ ID NO: 18          moltype = DNA   length = 25
FEATURE                Location/Qualifiers
source                 1..25
                       mol_type = other DNA
                       organism = synthetic construct
SEQUENCE: 18
atcagaagtt ttcacgccga ttaat                                              25

SEQ ID NO: 19          moltype = DNA   length = 25
FEATURE                Location/Qualifiers
source                 1..25
                       mol_type = other DNA
                       organism = synthetic construct
SEQUENCE: 19
ttttcacgcc gattaatcca attac                                              25

SEQ ID NO: 20          moltype = DNA   length = 25
FEATURE                Location/Qualifiers
source                 1..25
                       mol_type = other DNA
```

```
                                    organism = synthetic construct
SEQUENCE: 20
ccgattaatc caattacgat aactg                                              25

SEQ ID NO: 21           moltype = DNA   length = 25
FEATURE                 Location/Qualifiers
source                  1..25
                        mol_type = other DNA
                        organism = synthetic construct
SEQUENCE: 21
acatgtgtta cctgtacaaa cgaat                                              25

SEQ ID NO: 22           moltype = DNA   length = 25
FEATURE                 Location/Qualifiers
source                  1..25
                        mol_type = other DNA
                        organism = synthetic construct
SEQUENCE: 22
tgtacaaacg aataaaatct tcata                                              25

SEQ ID NO: 23           moltype = DNA   length = 25
FEATURE                 Location/Qualifiers
source                  1..25
                        mol_type = other DNA
                        organism = synthetic construct
SEQUENCE: 23
taaaatcttc atagttcaca tcctt                                              25

SEQ ID NO: 24           moltype = DNA   length = 25
FEATURE                 Location/Qualifiers
source                  1..25
                        mol_type = other DNA
                        organism = synthetic construct
SEQUENCE: 24
agttcacatc ctttaataat gtgat                                              25

SEQ ID NO: 25           moltype = DNA   length = 25
FEATURE                 Location/Qualifiers
source                  1..25
                        mol_type = other DNA
                        organism = synthetic construct
SEQUENCE: 25
ttaataatgt gattacctgc agctt                                              25

SEQ ID NO: 26           moltype = DNA   length = 25
FEATURE                 Location/Qualifiers
source                  1..25
                        mol_type = other DNA
                        organism = synthetic construct
SEQUENCE: 26
ttacctgcag cttttaacat gcgat                                              25

SEQ ID NO: 27           moltype = DNA   length = 25
FEATURE                 Location/Qualifiers
source                  1..25
                        mol_type = other DNA
                        organism = synthetic construct
SEQUENCE: 27
tttaacatgc gattcataat tgctt                                              25

SEQ ID NO: 28           moltype = DNA   length = 25
FEATURE                 Location/Qualifiers
source                  1..25
                        mol_type = other DNA
                        organism = synthetic construct
SEQUENCE: 28
ttcataattg cttctgtatt atcat                                              25

SEQ ID NO: 29           moltype = DNA   length = 25
FEATURE                 Location/Qualifiers
source                  1..25
                        mol_type = other DNA
                        organism = synthetic construct
SEQUENCE: 29
tctgtattat cattcagctc aaagc                                              25

SEQ ID NO: 30           moltype = DNA   length = 25
FEATURE                 Location/Qualifiers
source                  1..25
```

```
SEQ ID NO: 30                 (continued)
                              mol_type = other DNA
                              organism = synthetic construct
SEQUENCE: 30
ttcagctcaa agccgtatat atacg                                          25

SEQ ID NO: 31                 moltype = DNA  length = 25
FEATURE                       Location/Qualifiers
source                        1..25
                              mol_type = other DNA
                              organism = synthetic construct
SEQUENCE: 31
ccgtatatat acgccgctga aatat                                          25

SEQ ID NO: 32                 moltype = DNA  length = 25
FEATURE                       Location/Qualifiers
source                        1..25
                              mol_type = other DNA
                              organism = synthetic construct
SEQUENCE: 32
gccgctgaaa tattttcatt ttcat                                          25

SEQ ID NO: 33                 moltype = DNA  length = 25
FEATURE                       Location/Qualifiers
source                        1..25
                              mol_type = other DNA
                              organism = synthetic construct
SEQUENCE: 33
ttttcatttt catcaagtga atgta                                          25

SEQ ID NO: 34                 moltype = DNA  length = 25
FEATURE                       Location/Qualifiers
source                        1..25
                              mol_type = other DNA
                              organism = synthetic construct
SEQUENCE: 34
tcaagtgaat gtaacacatc ataaa                                          25

SEQ ID NO: 35                 moltype = DNA  length = 25
FEATURE                       Location/Qualifiers
source                        1..25
                              mol_type = other DNA
                              organism = synthetic construct
SEQUENCE: 35
aacacatcat aaagattatg acttg                                          25

SEQ ID NO: 36                 moltype = DNA  length = 25
FEATURE                       Location/Qualifiers
source                        1..25
                              mol_type = other DNA
                              organism = synthetic construct
SEQUENCE: 36
agattatgac ttgcttgttt aacat                                          25

SEQ ID NO: 37                 moltype = DNA  length = 25
FEATURE                       Location/Qualifiers
source                        1..25
                              mol_type = other DNA
                              organism = synthetic construct
SEQUENCE: 37
gcttgtttaa catcattgtc atcct                                          25

SEQ ID NO: 38                 moltype = DNA  length = 25
FEATURE                       Location/Qualifiers
source                        1..25
                              mol_type = other DNA
                              organism = synthetic construct
SEQUENCE: 38
tcattgtcat cctgacataa ttgaa                                          25

SEQ ID NO: 39                 moltype = DNA  length = 25
FEATURE                       Location/Qualifiers
source                        1..25
                              mol_type = other DNA
                              organism = synthetic construct
SEQUENCE: 39
tgacataatt gaatgaattg cgctt                                          25

SEQ ID NO: 40                 moltype = DNA  length = 25
FEATURE                       Location/Qualifiers
```

```
source                  1..25
                        mol_type = other DNA
                        organism = synthetic construct
SEQUENCE: 40
atgaattgcg cttcacttgg tataa                                              25

SEQ ID NO: 41           moltype = DNA   length = 25
FEATURE                 Location/Qualifiers
source                  1..25
                        mol_type = other DNA
                        organism = synthetic construct
SEQUENCE: 41
ggatgctaga cagttagcat gtatt                                              25

SEQ ID NO: 42           moltype = DNA   length = 25
FEATURE                 Location/Qualifiers
source                  1..25
                        mol_type = other DNA
                        organism = synthetic construct
SEQUENCE: 42
acagttagca tgtattgtca gagaa                                              25

SEQ ID NO: 43           moltype = DNA   length = 25
FEATURE                 Location/Qualifiers
source                  1..25
                        mol_type = other DNA
                        organism = synthetic construct
SEQUENCE: 43
atgtattgtc agagaaacac cttat                                              25

SEQ ID NO: 44           moltype = DNA   length = 25
FEATURE                 Location/Qualifiers
source                  1..25
                        mol_type = other DNA
                        organism = synthetic construct
SEQUENCE: 44
cagagaaaca ccttatattg caaac                                              25

SEQ ID NO: 45           moltype = DNA   length = 25
FEATURE                 Location/Qualifiers
source                  1..25
                        mol_type = other DNA
                        organism = synthetic construct
SEQUENCE: 45
accttatatt gcaaacaatg gggtg                                              25

SEQ ID NO: 46           moltype = DNA   length = 25
FEATURE                 Location/Qualifiers
source                  1..25
                        mol_type = other DNA
                        organism = synthetic construct
SEQUENCE: 46
tgcaaacaat ggggtgacta ttgtt                                              25

SEQ ID NO: 47           moltype = DNA   length = 25
FEATURE                 Location/Qualifiers
source                  1..25
                        mol_type = other DNA
                        organism = synthetic construct
SEQUENCE: 47
tggggtgact attgttactg gtgca                                              25

SEQ ID NO: 48           moltype = DNA   length = 25
FEATURE                 Location/Qualifiers
source                  1..25
                        mol_type = other DNA
                        organism = synthetic construct
SEQUENCE: 48
tattgttact ggtgcattgg ttaat                                              25

SEQ ID NO: 49           moltype = DNA   length = 25
FEATURE                 Location/Qualifiers
source                  1..25
                        mol_type = other DNA
                        organism = synthetic construct
SEQUENCE: 49
tggtgcattg gttaatccta atcca                                              25

SEQ ID NO: 50           moltype = DNA   length = 25
```

```
FEATURE                  Location/Qualifiers
source                   1..25
                         mol_type = other DNA
                         organism = synthetic construct
SEQUENCE: 50
ggttaatcct aatccaattg atcga                                           25

SEQ ID NO: 51            moltype = DNA   length = 25
FEATURE                  Location/Qualifiers
source                   1..25
                         mol_type = other DNA
                         organism = synthetic construct
SEQUENCE: 51
taatccaatt gatcgacata ttaca                                           25

SEQ ID NO: 52            moltype = DNA   length = 25
FEATURE                  Location/Qualifiers
source                   1..25
                         mol_type = other DNA
                         organism = synthetic construct
SEQUENCE: 52
tgatcgacat attacagttg atagt                                           25

SEQ ID NO: 53            moltype = DNA   length = 25
FEATURE                  Location/Qualifiers
source                   1..25
                         mol_type = other DNA
                         organism = synthetic construct
SEQUENCE: 53
tattacagtt gatagttata tcgaa                                           25

SEQ ID NO: 54            moltype = DNA   length = 25
FEATURE                  Location/Qualifiers
source                   1..25
                         mol_type = other DNA
                         organism = synthetic construct
SEQUENCE: 54
tgatagttat atcgaatggg ttaat                                           25

SEQ ID NO: 55            moltype = DNA   length = 25
FEATURE                  Location/Qualifiers
source                   1..25
                         mol_type = other DNA
                         organism = synthetic construct
SEQUENCE: 55
tatcgaatgg gttaatggtg agtta                                           25

SEQ ID NO: 56            moltype = DNA   length = 25
FEATURE                  Location/Qualifiers
source                   1..25
                         mol_type = other DNA
                         organism = synthetic construct
SEQUENCE: 56
ggttaatggt gagttaaata ataga                                           25

SEQ ID NO: 57            moltype = DNA   length = 25
FEATURE                  Location/Qualifiers
source                   1..25
                         mol_type = other DNA
                         organism = synthetic construct
SEQUENCE: 57
tgagttaaat aatagaggta tatta                                           25

SEQ ID NO: 58            moltype = DNA   length = 25
FEATURE                  Location/Qualifiers
source                   1..25
                         mol_type = other DNA
                         organism = synthetic construct
SEQUENCE: 58
taatagaggt atattaacct ttatt                                           25

SEQ ID NO: 59            moltype = DNA   length = 25
FEATURE                  Location/Qualifiers
source                   1..25
                         mol_type = other DNA
                         organism = synthetic construct
SEQUENCE: 59
tatattaacc tttattcaaa attat                                           25
```

| | | |
|---|---|---|
| SEQ ID NO: 60 | moltype = DNA length = 25 | |
| FEATURE | Location/Qualifiers | |
| source | 1..25 | |
| | mol_type = other DNA | |
| | organism = synthetic construct | |
| SEQUENCE: 60 | | |
| ctttattcaa aattatagtc gacaa | | 25 |
| | | |
| SEQ ID NO: 61 | moltype = DNA length = 25 | |
| FEATURE | Location/Qualifiers | |
| source | 1..25 | |
| | mol_type = other DNA | |
| | organism = synthetic construct | |
| SEQUENCE: 61 | | |
| gatcaacacc accctggcgg tgatg | | 25 |
| | | |
| SEQ ID NO: 62 | moltype = DNA length = 25 | |
| FEATURE | Location/Qualifiers | |
| source | 1..25 | |
| | mol_type = other DNA | |
| | organism = synthetic construct | |
| SEQUENCE: 62 | | |
| caccctggcg gtgatgttcg gctcg | | 25 |
| | | |
| SEQ ID NO: 63 | moltype = DNA length = 25 | |
| FEATURE | Location/Qualifiers | |
| source | 1..25 | |
| | mol_type = other DNA | |
| | organism = synthetic construct | |
| SEQUENCE: 63 | | |
| ggtgatgttc ggctcggact acatc | | 25 |
| | | |
| SEQ ID NO: 64 | moltype = DNA length = 25 | |
| FEATURE | Location/Qualifiers | |
| source | 1..25 | |
| | mol_type = other DNA | |
| | organism = synthetic construct | |
| SEQUENCE: 64 | | |
| cggctcggac tacatcggcg acttc | | 25 |
| | | |
| SEQ ID NO: 65 | moltype = DNA length = 25 | |
| FEATURE | Location/Qualifiers | |
| source | 1..25 | |
| | mol_type = other DNA | |
| | organism = synthetic construct | |
| SEQUENCE: 65 | | |
| ctacatcggc gacttcatgc acggc | | 25 |
| | | |
| SEQ ID NO: 66 | moltype = DNA length = 25 | |
| FEATURE | Location/Qualifiers | |
| source | 1..25 | |
| | mol_type = other DNA | |
| | organism = synthetic construct | |
| SEQUENCE: 66 | | |
| cgacttcatg cacggcagcc aggtg | | 25 |
| | | |
| SEQ ID NO: 67 | moltype = DNA length = 25 | |
| FEATURE | Location/Qualifiers | |
| source | 1..25 | |
| | mol_type = other DNA | |
| | organism = synthetic construct | |
| SEQUENCE: 67 | | |
| gcacggcagc caggtgcgca aggtg | | 25 |
| | | |
| SEQ ID NO: 68 | moltype = DNA length = 25 | |
| FEATURE | Location/Qualifiers | |
| source | 1..25 | |
| | mol_type = other DNA | |
| | organism = synthetic construct | |
| SEQUENCE: 68 | | |
| ccaggtgcgc aaggtggtgg tccag | | 25 |
| | | |
| SEQ ID NO: 69 | moltype = DNA length = 25 | |
| FEATURE | Location/Qualifiers | |
| source | 1..25 | |
| | mol_type = other DNA | |
| | organism = synthetic construct | |
| SEQUENCE: 69 | | |
| caaggtggtg gtccaggccg acggc | | 25 |

| | | |
|---|---|---|
| SEQ ID NO: 70<br>FEATURE<br>source | moltype = DNA   length = 25<br>Location/Qualifiers<br>1..25<br>mol_type = other DNA<br>organism = synthetic construct | |
| SEQUENCE: 70<br>ggtccaggcc gacggcgcca agcgc | | 25 |
| SEQ ID NO: 71<br>FEATURE<br>source | moltype = DNA   length = 25<br>Location/Qualifiers<br>1..25<br>mol_type = other DNA<br>organism = synthetic construct | |
| SEQUENCE: 71<br>cgacggcgcc aagcgcctgg gcatc | | 25 |
| SEQ ID NO: 72<br>FEATURE<br>source | moltype = DNA   length = 25<br>Location/Qualifiers<br>1..25<br>mol_type = other DNA<br>organism = synthetic construct | |
| SEQUENCE: 72<br>caagcgcctg ggcatcgacg acatc | | 25 |
| SEQ ID NO: 73<br>FEATURE<br>source | moltype = DNA   length = 25<br>Location/Qualifiers<br>1..25<br>mol_type = other DNA<br>organism = synthetic construct | |
| SEQUENCE: 73<br>gggcatcgac gacatcggcc ggctt | | 25 |
| SEQ ID NO: 74<br>FEATURE<br>source | moltype = DNA   length = 25<br>Location/Qualifiers<br>1..25<br>mol_type = other DNA<br>organism = synthetic construct | |
| SEQUENCE: 74<br>cgacatcggc cggcttcacg tgcgc | | 25 |
| SEQ ID NO: 75<br>FEATURE<br>source | moltype = DNA   length = 25<br>Location/Qualifiers<br>1..25<br>mol_type = other DNA<br>organism = synthetic construct | |
| SEQUENCE: 75<br>ccggcttcac gtgcgcaacg agcag | | 25 |
| SEQ ID NO: 76<br>FEATURE<br>source | moltype = DNA   length = 25<br>Location/Qualifiers<br>1..25<br>mol_type = other DNA<br>organism = synthetic construct | |
| SEQUENCE: 76<br>cgtgcgcaac gagcagggcg agatg | | 25 |
| SEQ ID NO: 77<br>FEATURE<br>source | moltype = DNA   length = 25<br>Location/Qualifiers<br>1..25<br>mol_type = other DNA<br>organism = synthetic construct | |
| SEQUENCE: 77<br>cgagcagggc gagatggtgc cgctg | | 25 |
| SEQ ID NO: 78<br>FEATURE<br>source | moltype = DNA   length = 25<br>Location/Qualifiers<br>1..25<br>mol_type = other DNA<br>organism = synthetic construct | |
| SEQUENCE: 78<br>cgagatggtg ccgctggcga cgttc | | 25 |
| SEQ ID NO: 79<br>FEATURE<br>source | moltype = DNA   length = 25<br>Location/Qualifiers<br>1..25<br>mol_type = other DNA<br>organism = synthetic construct | |
| SEQUENCE: 79 | | |

```
gccgctggcg acgttcgcca aggcc                                       25

SEQ ID NO: 80          moltype = DNA   length = 25
FEATURE                Location/Qualifiers
source                 1..25
                       mol_type = other DNA
                       organism = synthetic construct
SEQUENCE: 80
gacgttcgcc aaggccgcct ggacc                                       25

SEQ ID NO: 81          moltype = DNA   length = 25
FEATURE                Location/Qualifiers
source                 1..25
                       mol_type = other DNA
                       organism = synthetic construct
SEQUENCE: 81
tactatgtcg caagtgaaac aattg                                       25

SEQ ID NO: 82          moltype = DNA   length = 25
FEATURE                Location/Qualifiers
source                 1..25
                       mol_type = other DNA
                       organism = synthetic construct
SEQUENCE: 82
gcaagtgaaa caattgaggt taaag                                       25

SEQ ID NO: 83          moltype = DNA   length = 25
FEATURE                Location/Qualifiers
source                 1..25
                       mol_type = other DNA
                       organism = synthetic construct
SEQUENCE: 83
acaattgagg ttaaagacct tatag                                       25

SEQ ID NO: 84          moltype = DNA   length = 25
FEATURE                Location/Qualifiers
source                 1..25
                       mol_type = other DNA
                       organism = synthetic construct
SEQUENCE: 84
gttaaagacc ttatagattt cttac                                       25

SEQ ID NO: 85          moltype = DNA   length = 25
FEATURE                Location/Qualifiers
source                 1..25
                       mol_type = other DNA
                       organism = synthetic construct
SEQUENCE: 85
cttatagatt tcttacaaga acatt                                       25

SEQ ID NO: 86          moltype = DNA   length = 25
FEATURE                Location/Qualifiers
source                 1..25
                       mol_type = other DNA
                       organism = synthetic construct
SEQUENCE: 86
ttcttacaag aacatttagc aaaat                                       25

SEQ ID NO: 87          moltype = DNA   length = 25
FEATURE                Location/Qualifiers
source                 1..25
                       mol_type = other DNA
                       organism = synthetic construct
SEQUENCE: 87
gaacatttag caaaatataa agttc                                       25

SEQ ID NO: 88          moltype = DNA   length = 25
FEATURE                Location/Qualifiers
source                 1..25
                       mol_type = other DNA
                       organism = synthetic construct
SEQUENCE: 88
gcaaaatata agttcctaa gatat                                        25

SEQ ID NO: 89          moltype = DNA   length = 25
FEATURE                Location/Qualifiers
source                 1..25
                       mol_type = other DNA
                       organism = synthetic construct
```

```
SEQUENCE: 89
aaagttccta agatatatca acgcg                                              25

SEQ ID NO: 90           moltype = DNA   length = 25
FEATURE                 Location/Qualifiers
source                  1..25
                        mol_type = other DNA
                        organism = synthetic construct
SEQUENCE: 90
aagatatatc aacgcgtcaa tgcat                                              25

SEQ ID NO: 91           moltype = DNA   length = 25
FEATURE                 Location/Qualifiers
source                  1..25
                        mol_type = other DNA
                        organism = synthetic construct
SEQUENCE: 91
caacgcgtca atgcattacc ttata                                              25

SEQ ID NO: 92           moltype = DNA   length = 25
FEATURE                 Location/Qualifiers
source                  1..25
                        mol_type = other DNA
                        organism = synthetic construct
SEQUENCE: 92
aatgcattac cttatacttc tactg                                              25

SEQ ID NO: 93           moltype = DNA   length = 25
FEATURE                 Location/Qualifiers
source                  1..25
                        mol_type = other DNA
                        organism = synthetic construct
SEQUENCE: 93
ccttatactt ctactggaaa attac                                              25

SEQ ID NO: 94           moltype = DNA   length = 25
FEATURE                 Location/Qualifiers
source                  1..25
                        mol_type = other DNA
                        organism = synthetic construct
SEQUENCE: 94
tctactggaa aattacaacg taata                                              25

SEQ ID NO: 95           moltype = DNA   length = 25
FEATURE                 Location/Qualifiers
source                  1..25
                        mol_type = other DNA
                        organism = synthetic construct
SEQUENCE: 95
aaattacaac gtaataaagt tggaa                                              25

SEQ ID NO: 96           moltype = DNA   length = 25
FEATURE                 Location/Qualifiers
source                  1..25
                        mol_type = other DNA
                        organism = synthetic construct
SEQUENCE: 96
cgtaataaag ttggaactga ggatc                                              25

SEQ ID NO: 97           moltype = DNA   length = 25
FEATURE                 Location/Qualifiers
source                  1..25
                        mol_type = other DNA
                        organism = synthetic construct
SEQUENCE: 97
gttggaactg aggatcatta aatga                                              25

SEQ ID NO: 98           moltype = DNA   length = 25
FEATURE                 Location/Qualifiers
source                  1..25
                        mol_type = other DNA
                        organism = synthetic construct
SEQUENCE: 98
gaggatcatt aaatgaaaat tattg                                              25

SEQ ID NO: 99           moltype = DNA   length = 25
FEATURE                 Location/Qualifiers
source                  1..25
                        mol_type = other DNA
```

```
                            organism = synthetic construct
SEQUENCE: 99
taaatgaaaa ttattgatat acaat                                              25

SEQ ID NO: 100              moltype = DNA   length = 25
FEATURE                     Location/Qualifiers
source                      1..25
                            mol_type = other DNA
                            organism = synthetic construct
SEQUENCE: 100
attattgata tacaattta ttact                                               25

SEQ ID NO: 101              moltype = DNA   length = 25
FEATURE                     Location/Qualifiers
source                      1..25
                            mol_type = other DNA
                            organism = synthetic construct
SEQUENCE: 101
gttgttcgcc agagtcaagc tggaa                                              25

SEQ ID NO: 102              moltype = DNA   length = 25
FEATURE                     Location/Qualifiers
source                      1..25
                            mol_type = other DNA
                            organism = synthetic construct
SEQUENCE: 102
cgccagagtc aagctggaaa ccggc                                              25

SEQ ID NO: 103              moltype = DNA   length = 25
FEATURE                     Location/Qualifiers
source                      1..25
                            mol_type = other DNA
                            organism = synthetic construct
SEQUENCE: 103
agtcaagctg gaaaccggcg cgccg                                              25

SEQ ID NO: 104              moltype = DNA   length = 25
FEATURE                     Location/Qualifiers
source                      1..25
                            mol_type = other DNA
                            organism = synthetic construct
SEQUENCE: 104
gctggaaacc ggcgcgccgc aggcc                                              25

SEQ ID NO: 105              moltype = DNA   length = 25
FEATURE                     Location/Qualifiers
source                      1..25
                            mol_type = other DNA
                            organism = synthetic construct
SEQUENCE: 105
cgaccaatcg attggcaccg atcaa                                              25

SEQ ID NO: 106              moltype = DNA   length = 25
FEATURE                     Location/Qualifiers
source                      1..25
                            mol_type = other DNA
                            organism = synthetic construct
SEQUENCE: 106
atcgattggc accgatcaaa accgg                                              25

SEQ ID NO: 107              moltype = DNA   length = 25
FEATURE                     Location/Qualifiers
source                      1..25
                            mol_type = other DNA
                            organism = synthetic construct
SEQUENCE: 107
tggcaccgat caaaaccggc gctat                                              25

SEQ ID NO: 108              moltype = DNA   length = 25
FEATURE                     Location/Qualifiers
source                      1..25
                            mol_type = other DNA
                            organism = synthetic construct
SEQUENCE: 108
cgatcaaaac cggcgctatg tcctg                                              25

SEQ ID NO: 109              moltype = DNA   length = 25
FEATURE                     Location/Qualifiers
source                      1..25
```

```
                        mol_type = other DNA
                        organism = synthetic construct
SEQUENCE: 109
aaaccggcgc tatgtcctgg tcgtc                                              25

SEQ ID NO: 110          moltype = DNA  length = 25
FEATURE                 Location/Qualifiers
source                  1..25
                        mol_type = other DNA
                        organism = synthetic construct
SEQUENCE: 110
gcgctatgtc ctggtcgtcg atgag                                              25

SEQ ID NO: 111          moltype = DNA  length = 25
FEATURE                 Location/Qualifiers
source                  1..25
                        mol_type = other DNA
                        organism = synthetic construct
SEQUENCE: 111
tgtcctggtc gtcgatgaga atgac                                              25

SEQ ID NO: 112          moltype = DNA  length = 25
FEATURE                 Location/Qualifiers
source                  1..25
                        mol_type = other DNA
                        organism = synthetic construct
SEQUENCE: 112
gaatgacaaa accgaatacc gcccc                                              25

SEQ ID NO: 113          moltype = DNA  length = 25
FEATURE                 Location/Qualifiers
source                  1..25
                        mol_type = other DNA
                        organism = synthetic construct
SEQUENCE: 113
caaaaccgaa taccgccccg ttgaa                                              25

SEQ ID NO: 114          moltype = DNA  length = 25
FEATURE                 Location/Qualifiers
source                  1..25
                        mol_type = other DNA
                        organism = synthetic construct
SEQUENCE: 114
cgaataccgc cccgttgaac ttggc                                              25

SEQ ID NO: 115          moltype = DNA  length = 25
FEATURE                 Location/Qualifiers
source                  1..25
                        mol_type = other DNA
                        organism = synthetic construct
SEQUENCE: 115
ccgccccgtt gaacttggcc cggtc                                              25

SEQ ID NO: 116          moltype = DNA  length = 25
FEATURE                 Location/Qualifiers
source                  1..25
                        mol_type = other DNA
                        organism = synthetic construct
SEQUENCE: 116
cgttgaactt ggcccggtcg ttgaa                                              25

SEQ ID NO: 117          moltype = DNA  length = 25
FEATURE                 Location/Qualifiers
source                  1..25
                        mol_type = other DNA
                        organism = synthetic construct
SEQUENCE: 117
acttggcccg gtcgttgaag gactg                                              25

SEQ ID NO: 118          moltype = DNA  length = 25
FEATURE                 Location/Qualifiers
source                  1..25
                        mol_type = other DNA
                        organism = synthetic construct
SEQUENCE: 118
cccggtcgtt gaaggactgc gcgtg                                              25

SEQ ID NO: 119          moltype = DNA  length = 25
FEATURE                 Location/Qualifiers
```

```
source                  1..25
                        mol_type = other DNA
                        organism = synthetic construct
SEQUENCE: 119
cgttgaagga ctgcgcgtga tagag                                              25

SEQ ID NO: 120          moltype = DNA   length = 25
FEATURE                 Location/Qualifiers
source                  1..25
                        mol_type = other DNA
                        organism = synthetic construct
SEQUENCE: 120
aggactgcgc gtgatagagc acggc                                              25

SEQ ID NO: 121          moltype = DNA   length = 25
FEATURE                 Location/Qualifiers
source                  1..25
                        mol_type = other DNA
                        organism = synthetic construct
SEQUENCE: 121
tgaacttgcc tttgccgccg ggatc                                              25

SEQ ID NO: 122          moltype = DNA   length = 25
FEATURE                 Location/Qualifiers
source                  1..25
                        mol_type = other DNA
                        organism = synthetic construct
SEQUENCE: 122
ctttgccgcc gggatcacgc cggtt                                              25

SEQ ID NO: 123          moltype = DNA   length = 25
FEATURE                 Location/Qualifiers
source                  1..25
                        mol_type = other DNA
                        organism = synthetic construct
SEQUENCE: 123
cgggatcacg ccggttgggg tcagc                                              25

SEQ ID NO: 124          moltype = DNA   length = 25
FEATURE                 Location/Qualifiers
source                  1..25
                        mol_type = other DNA
                        organism = synthetic construct
SEQUENCE: 124
gccggttggg gtcagcagct attcc                                              25

SEQ ID NO: 125          moltype = DNA   length = 25
FEATURE                 Location/Qualifiers
source                  1..25
                        mol_type = other DNA
                        organism = synthetic construct
SEQUENCE: 125
ggtcagcagc tattccgact atcct                                              25

SEQ ID NO: 126          moltype = DNA   length = 25
FEATURE                 Location/Qualifiers
source                  1..25
                        mol_type = other DNA
                        organism = synthetic construct
SEQUENCE: 126
ctattccgac tatcctccac aagcg                                              25

SEQ ID NO: 127          moltype = DNA   length = 25
FEATURE                 Location/Qualifiers
source                  1..25
                        mol_type = other DNA
                        organism = synthetic construct
SEQUENCE: 127
ctatcctcca caagcgcaaa agatt                                              25

SEQ ID NO: 128          moltype = DNA   length = 25
FEATURE                 Location/Qualifiers
source                  1..25
                        mol_type = other DNA
                        organism = synthetic construct
SEQUENCE: 128
acaagcgcaa aagattgagc aggtt                                              25

SEQ ID NO: 129          moltype = DNA   length = 25
```

```
FEATURE                 Location/Qualifiers
source                  1..25
                        mol_type = other DNA
                        organism = synthetic construct
SEQUENCE: 129
aaagattgag caggtttcca cctgg                                               25

SEQ ID NO: 130          moltype = DNA   length = 25
FEATURE                 Location/Qualifiers
source                  1..25
                        mol_type = other DNA
                        organism = synthetic construct
SEQUENCE: 130
gcaggtttcc acctggcagg ggatg                                               25

SEQ ID NO: 131          moltype = DNA   length = 25
FEATURE                 Location/Qualifiers
source                  1..25
                        mol_type = other DNA
                        organism = synthetic construct
SEQUENCE: 131
cacctggcag gggatgaatc tggaa                                               25

SEQ ID NO: 132          moltype = DNA   length = 25
FEATURE                 Location/Qualifiers
source                  1..25
                        mol_type = other DNA
                        organism = synthetic construct
SEQUENCE: 132
ggggatgaat ctggaacgca ttgtc                                               25

SEQ ID NO: 133          moltype = DNA   length = 25
FEATURE                 Location/Qualifiers
source                  1..25
                        mol_type = other DNA
                        organism = synthetic construct
SEQUENCE: 133
tctggaacgc attgtcgcgc tgaaa                                               25

SEQ ID NO: 134          moltype = DNA   length = 25
FEATURE                 Location/Qualifiers
source                  1..25
                        mol_type = other DNA
                        organism = synthetic construct
SEQUENCE: 134
cattgtcgcg ctgaaacccg atctg                                               25

SEQ ID NO: 135          moltype = DNA   length = 25
FEATURE                 Location/Qualifiers
source                  1..25
                        mol_type = other DNA
                        organism = synthetic construct
SEQUENCE: 135
gctgaaaccc gatctggtga ttgcc                                               25

SEQ ID NO: 136          moltype = DNA   length = 25
FEATURE                 Location/Qualifiers
source                  1..25
                        mol_type = other DNA
                        organism = synthetic construct
SEQUENCE: 136
cgatctggtg attgcctggc gtgga                                               25

SEQ ID NO: 137          moltype = DNA   length = 25
FEATURE                 Location/Qualifiers
source                  1..25
                        mol_type = other DNA
                        organism = synthetic construct
SEQUENCE: 137
gattgcctgg cgtggaggta atgcc                                               25

SEQ ID NO: 138          moltype = DNA   length = 25
FEATURE                 Location/Qualifiers
source                  1..25
                        mol_type = other DNA
                        organism = synthetic construct
SEQUENCE: 138
gcgtggaggt aatgccgagc ggcag                                               25
```

| | | |
|---|---|---|
| SEQ ID NO: 139 | moltype = DNA length = 25 | |
| FEATURE | Location/Qualifiers | |
| source | 1..25 | |
| | mol_type = other DNA | |
| | organism = synthetic construct | |
| SEQUENCE: 139 | | |
| taatgccgag cggcaggttg accag | | 25 |
| | | |
| SEQ ID NO: 140 | moltype = DNA length = 25 | |
| FEATURE | Location/Qualifiers | |
| source | 1..25 | |
| | mol_type = other DNA | |
| | organism = synthetic construct | |
| SEQUENCE: 140 | | |
| gcggcaggtt gaccagctgg cttcg | | 25 |
| | | |
| SEQ ID NO: 141 | moltype = DNA length = 25 | |
| FEATURE | Location/Qualifiers | |
| source | 1..25 | |
| | mol_type = other DNA | |
| | organism = synthetic construct | |
| SEQUENCE: 141 | | |
| cggaggttct gctgacctag cggga | | 25 |
| | | |
| SEQ ID NO: 142 | moltype = DNA length = 25 | |
| FEATURE | Location/Qualifiers | |
| source | 1..25 | |
| | mol_type = other DNA | |
| | organism = synthetic construct | |
| SEQUENCE: 142 | | |
| aggttctgct gacctagcgg gatcg | | 25 |
| | | |
| SEQ ID NO: 143 | moltype = DNA length = 25 | |
| FEATURE | Location/Qualifiers | |
| source | 1..25 | |
| | mol_type = other DNA | |
| | organism = synthetic construct | |
| SEQUENCE: 143 | | |
| ttctgctgac ctagcgggat cgaac | | 25 |
| | | |
| SEQ ID NO: 144 | moltype = DNA length = 25 | |
| FEATURE | Location/Qualifiers | |
| source | 1..25 | |
| | mol_type = other DNA | |
| | organism = synthetic construct | |
| SEQUENCE: 144 | | |
| tgctgaccta gcgggatcga acaaa | | 25 |
| | | |
| SEQ ID NO: 145 | moltype = DNA length = 25 | |
| FEATURE | Location/Qualifiers | |
| source | 1..25 | |
| | mol_type = other DNA | |
| | organism = synthetic construct | |
| SEQUENCE: 145 | | |
| tgacctagcg ggatcgaaca aaacg | | 25 |
| | | |
| SEQ ID NO: 146 | moltype = DNA length = 25 | |
| FEATURE | Location/Qualifiers | |
| source | 1..25 | |
| | mol_type = other DNA | |
| | organism = synthetic construct | |
| SEQUENCE: 146 | | |
| cctagcggga tcgaacaaaa cgact | | 25 |
| | | |
| SEQ ID NO: 147 | moltype = DNA length = 25 | |
| FEATURE | Location/Qualifiers | |
| source | 1..25 | |
| | mol_type = other DNA | |
| | organism = synthetic construct | |
| SEQUENCE: 147 | | |
| agcgggatcg aacaaaacga ctatt | | 25 |
| | | |
| SEQ ID NO: 148 | moltype = DNA length = 25 | |
| FEATURE | Location/Qualifiers | |
| source | 1..25 | |
| | mol_type = other DNA | |
| | organism = synthetic construct | |
| SEQUENCE: 148 | | |
| gtcagtaatg acgcacctga atata | | 25 |

| SEQ ID NO: 149 | moltype = DNA length = 25 |
| --- | --- |
| FEATURE | Location/Qualifiers |
| source | 1..25 |
| | mol_type = other DNA |
| | organism = synthetic construct |

SEQUENCE: 149
agtaatgacg cacctgaata tattc 25

| SEQ ID NO: 150 | moltype = DNA length = 25 |
| --- | --- |
| FEATURE | Location/Qualifiers |
| source | 1..25 |
| | mol_type = other DNA |
| | organism = synthetic construct |

SEQUENCE: 150
cgcgtaggat catatttaac cagcg 25

| SEQ ID NO: 151 | moltype = DNA length = 25 |
| --- | --- |
| FEATURE | Location/Qualifiers |
| source | 1..25 |
| | mol_type = other DNA |
| | organism = synthetic construct |

SEQUENCE: 151
gtaggatcat atttaaccag cgatt 25

| SEQ ID NO: 152 | moltype = DNA length = 25 |
| --- | --- |
| FEATURE | Location/Qualifiers |
| source | 1..25 |
| | mol_type = other DNA |
| | organism = synthetic construct |

SEQUENCE: 152
ggatcatatt taaccagcga ttatg 25

| SEQ ID NO: 153 | moltype = DNA length = 25 |
| --- | --- |
| FEATURE | Location/Qualifiers |
| source | 1..25 |
| | mol_type = other DNA |
| | organism = synthetic construct |

SEQUENCE: 153
tcatatttaa ccagcgatta tggac 25

| SEQ ID NO: 154 | moltype = DNA length = 25 |
| --- | --- |
| FEATURE | Location/Qualifiers |
| source | 1..25 |
| | mol_type = other DNA |
| | organism = synthetic construct |

SEQUENCE: 154
tatttaacca gcgattatgg acgcg 25

| SEQ ID NO: 155 | moltype = DNA length = 25 |
| --- | --- |
| FEATURE | Location/Qualifiers |
| source | 1..25 |
| | mol_type = other DNA |
| | organism = synthetic construct |

SEQUENCE: 155
ttaaccagcg attatggacg cgttg 25

| SEQ ID NO: 156 | moltype = DNA length = 25 |
| --- | --- |
| FEATURE | Location/Qualifiers |
| source | 1..25 |
| | mol_type = other DNA |
| | organism = synthetic construct |

SEQUENCE: 156
accagcgatt atggacgcgt tgatt 25

| SEQ ID NO: 157 | moltype = DNA length = 25 |
| --- | --- |
| FEATURE | Location/Qualifiers |
| source | 1..25 |
| | mol_type = other DNA |
| | organism = synthetic construct |

SEQUENCE: 157
ggtctacctt cagggttatc ttttg 25

| SEQ ID NO: 158 | moltype = DNA length = 22 |
| --- | --- |
| FEATURE | Location/Qualifiers |
| source | 1..22 |
| | mol_type = other DNA |
| | organism = synthetic construct |

SEQUENCE: 158 agtccttgtg gcaatcctgt ta                                            22

SEQ ID NO: 159          moltype = DNA   length = 21
FEATURE                 Location/Qualifiers
source                  1..21
                        mol_type = other DNA
                        organism = synthetic construct
SEQUENCE: 159
actttccgct aatgggctac g                                             21

SEQ ID NO: 160          moltype = DNA   length = 21
FEATURE                 Location/Qualifiers
source                  1..21
                        mol_type = other DNA
                        organism = synthetic construct
SEQUENCE: 160
tgtgccgagt aataaggtgg c                                             21

SEQ ID NO: 161          moltype = DNA   length = 21
FEATURE                 Location/Qualifiers
source                  1..21
                        mol_type = other DNA
                        organism = synthetic construct
SEQUENCE: 161
atgtgcgaaa acaaatgacg a                                             21

SEQ ID NO: 162          moltype = DNA   length = 25
FEATURE                 Location/Qualifiers
source                  1..25
                        mol_type = other DNA
                        organism = synthetic construct
SEQUENCE: 162
gcttctaaag ctatgccata ctctt                                         25

SEQ ID NO: 163          moltype = DNA   length = 17
FEATURE                 Location/Qualifiers
source                  1..17
                        mol_type = other DNA
                        organism = synthetic construct
SEQUENCE: 163
ggcgtgagca tggacga                                                  17

SEQ ID NO: 164          moltype = DNA   length = 19
FEATURE                 Location/Qualifiers
source                  1..19
                        mol_type = other DNA
                        organism = synthetic construct
SEQUENCE: 164
ccgttgtagc gggtcagtt                                                19

SEQ ID NO: 165          moltype = DNA   length = 20
FEATURE                 Location/Qualifiers
source                  1..20
                        mol_type = other DNA
                        organism = synthetic construct
SEQUENCE: 165
ggggtcagat tccagcactt                                               20

SEQ ID NO: 166          moltype = DNA   length = 20
FEATURE                 Location/Qualifiers
source                  1..20
                        mol_type = other DNA
                        organism = synthetic construct
SEQUENCE: 166
ttaggcgtcg taatcggaga                                               20

SEQ ID NO: 167          moltype = DNA   length = 20
FEATURE                 Location/Qualifiers
source                  1..20
                        mol_type = other DNA
                        organism = synthetic construct
SEQUENCE: 167
ctgtcacctg ggttgttcgc                                               20

SEQ ID NO: 168          moltype = DNA   length = 21
FEATURE                 Location/Qualifiers
source                  1..21
                        mol_type = other DNA
                        organism = synthetic construct

```
SEQUENCE: 168
gggaaagtca tgtcgcgtct c                                                                 21

SEQ ID NO: 169         moltype = DNA  length = 18
FEATURE                Location/Qualifiers
source                 1..18
                       mol_type = other DNA
                       organism = synthetic construct
SEQUENCE: 169
gctttctccc gccaacac                                                                     18

SEQ ID NO: 170         moltype = DNA  length = 23
FEATURE                Location/Qualifiers
source                 1..23
                       mol_type = other DNA
                       organism = synthetic construct
SEQUENCE: 170
catcgaccca catcactttt att                                                               23

SEQ ID NO: 171         moltype = DNA  length = 20
FEATURE                Location/Qualifiers
source                 1..20
                       mol_type = other DNA
                       organism = synthetic construct
SEQUENCE: 171
cgacaatcgg attcggttca                                                                   20

SEQ ID NO: 172         moltype = DNA  length = 21
FEATURE                Location/Qualifiers
source                 1..21
                       mol_type = other DNA
                       organism = synthetic construct
SEQUENCE: 172
tgttcgatcc cgctaggtca g                                                                 21

SEQ ID NO: 173         moltype = DNA  length = 20
FEATURE                Location/Qualifiers
source                 1..20
                       mol_type = other DNA
                       organism = synthetic construct
SEQUENCE: 173
tctggctaag gaacgggtct                                                                   20

SEQ ID NO: 174         moltype = DNA  length = 22
FEATURE                Location/Qualifiers
source                 1..22
                       mol_type = other DNA
                       organism = synthetic construct
SEQUENCE: 174
gcgtcttgtg agtgcagtct aa                                                                22
```

PROBES, MICROARRAY, PRIMERS, KIT AND APPLICATIONS FOR RAPID DETECTION OF CLINICAL OPHTHALMIC MICROORGANISMS

CROSS-REFERENCE TO RELATED APPLICATION

This application claims priority to Chinese Patent Application No. 202011604557.8, filed on Dec. 30, 2020, the contents of which are hereby incorporated by reference.

TECHNICAL FIELD

The disclosure relates to the technical field of microbial detection, in particular to probes, a microarray, primers, a kit and an application for rapid detection of clinical ophthalmic microorganisms.

STATEMENT REGARDING SEQUENCE LISTING

The sequence listing associated with this application is provided in text format in lieu of a paper copy and is hereby incorporated by reference into the specification. The name of the XML file containing the sequence listing is 22040TDFS-USP1-2022-7168-SL.xml. The XML file is 154,958 bytes; was created on Aug. 10, 2022; contains no new matter; and is being submitted electronically via EFS-Web.

BACKGROUND

Previously ophthalmic infections were identified by bacterial culture and smear staining, but there were problems of lengthy identification periods and insufficient positive rates. Ophthalmic infections progress rapidly and early and timely diagnosis is essential in terms of saving the patient's vision and mitigating damage. Morphological judgement alone can lead to misdiagnosis and failure of identifying the causative agent of the infection, only a suspected diagnosis can be made. Most cases of ophthalmic infections are mixed infections caused by a combination of pathogens with a complex bacterial flora. Conventional method of bacterial culture usually identifies only a single organism and provides limited guidance for subsequent treatment. 16S rDNA is a sequence encoding rRNA on bacterial chromosomes and is highly specific for sequencing bacteria. 16S rDNA sequencing offers a 100% detection for identifying pathogenic bacteria and allows for qualitative and quantitative identification of the main pathogenic groups for reference in clinical drug combinations; however, this technology is not yet available for large-scale clinical application in hospitals as it relies on large sequencing platforms and equipment; instead, it is still dependent on sequencing services provided by third-party companies, which is a cumbersome process with long lead times for returning results and cannot provide time-sensitive assistance for routine diagnosis.

SUMMARY

The present disclosure provides probes, a microarray and primers for rapid detection of clinical ophthalmic microorganisms. By combining molecular diagnostic sequencing technology with microarray technology, the present disclosure discloses a microarray that allows for the direct detection of common ophthalmic microorganisms in clinical pathogen laboratories with high specificity and a significant positive rate in detecting microorganisms present in ophthalmic clinical samples, improving both the accuracy and speed of detection, making the product suitable for large-scale clinical dissemination.

The disclosure provides probes for rapid detection of clinical ophthalmic microorganisms, where the probes include probes for detecting *Staphylococcus epidermidis*, probes for detecting *Staphylococcus aureus*, probes for detecting *Staphylococcus haemolyticus*, probes for detecting *Pseudomonas aeruginosa*, probes for detecting *Staphylococcus hominis*, probes for detecting *Serratia marcescens*, probes for detecting *Escherichia coli*, probes for detecting *Bacillus subtilis* and probes for detecting *Enterobacter cloacae* respectively;

the probes for detecting *Staphylococcus epidermidis* include probes with nucleotide sequences as shown in SEQ ID NO.1-20 respectively;

the probes for detecting *Staphylococcus aureus* include probes with nucleotide sequences as shown in SEQ ID NO.21-40 respectively;

the probes for detecting *Staphylococcus haemolyticus* include probes with nucleotide sequences as shown in SEQ ID NO.41-60 respectively;

the probes for detecting *Pseudomonas aeruginosa* include probes with nucleotide sequences as shown in SEQ ID NO.61-80 respectively;

the probes for detecting *Staphylococcus hominis* include probes with nucleotide sequences as shown in SEQ ID NO.81-100 respectively;

the probes for detecting *Serratia marcescens* include probes with nucleotide sequences as shown in SEQ ID NO.101-120 respectively;

the probes for detecting *Escherichia coli* include probes with nucleotide sequences as shown in SEQ ID NO.121-140 respectively;

the probes for detecting *Bacillus subtilis* include probes with nucleotide sequences as shown in SEQ ID NO.141-147 respectively; and the probes for detecting *Enterobacter cloacae* include probes with nucleotide sequences as shown in SEQ ID NO.148-156, respectively.

The disclosure also provides a microarray for rapid detection of clinical ophthalmic microorganisms, where the microarray is provided with probes as described in the above technical scheme.

The disclosure also provides primers for rapid detection of clinical ophthalmic microorganisms, where the primers include primers for detecting *Staphylococcus epidermidis, Staphylococcus aureus, Staphylococcus haemolyticus, Pseudomonas aeruginosa, Staphylococcus hominis, Serratia marcescens, Escherichia coli, Bacillus subtilis* and *Enterobacter cloacae* respectively;

the primers for detecting *Staphylococcus epidermidis* include a forward primer with a nucleotide sequence as shown in SEQ ID NO.157 and a reverse primer with a nucleotide sequence as shown in SEQ ID NO.158;

the primers for detecting *Staphylococcus aureus* include a forward primer with a nucleotide sequence as shown in SEQ ID NO.159 and a reverse primer with a nucleotide sequence as shown in SEQ ID NO.160;

the primers for detecting *Staphylococcus haemolyticus* include a forward primer with a nucleotide sequence as shown in SEQ ID NO.161 and a reverse primer with a nucleotide sequence as shown in SEQ ID NO.162;

the primers for detecting *Pseudomonas aeruginosa* include a forward primer with a nucleotide sequence as shown in SEQ ID NO.163 and a reverse primer with a nucleotide sequence as shown in SEQ ID NO.164;

the primers for detecting *Staphylococcus hominis* include a forward primer with a nucleotide sequence as shown in SEQ ID NO.165 and a reverse primer with a nucleotide sequence as shown in SEQ ID NO.166;

the primers for detecting *Serratia marcescens* include a forward primer with a nucleotide sequence as shown in SEQ ID NO.167 and a reverse primer with a nucleotide sequence as shown in SEQ ID NO.168;

the primers for detecting *Escherichia coli* include a forward primer with a nucleotide sequence as shown in SEQ ID NO.169 and a reverse primer with a nucleotide sequence as shown in SEQ ID NO.170;

the primers for detecting *Bacillus subtilis* include a forward primer with a nucleotide sequence as shown in SEQ ID NO.171 and a reverse primer with a nucleotide sequence as shown in SEQ ID NO.172; and the primers for detecting *Enterobacter cloacae* include a forward primer with a nucleotide sequence as shown in SEQ ID NO.173 and a reverse primer with a nucleotide sequence as shown in SEQ ID NO.174.

Optionally, the forward primers in above primers are all labelled with a fluorescent group at a 5' end; and optionally, the fluorescent group includes Cyanine 3 (Cy3).

The disclosure also provides a primer-probe set for rapid detection of clinical ophthalmic microorganisms, and the set includes the probe described in the above technical scheme and the primer described in the above technical scheme.

The disclosure also provides a kit for rapid detection of clinical ophthalmic microorganisms, including that microarray and primers described in the technical scheme above.

The present disclosure provides probes for rapid detection of clinical microorganisms in ophthalmology, where the whole genome of nine of the most common pathogenic bacteria in ophthalmic infectious diseases are aligned and sequences with >95% intra- and <75% interspecies homology are identified, and hybrid probes are constructed for the screened sequences as well as polymerase chain reaction (PCR) primers with fluorescent groups, which are subsequently synthesized on a gene microarray; the fluorescently labelled PCR primers are used to conduct PCR on the pathogenic bacteria to obtain fluorescent products, and the products are hybridized with the hybrid probes to achieve rapid identification of the pathogenic bacteria.

The microarray prepared by the probe of the present disclosure has the following advantages:

swift detection: the present disclosure achieves simple identification with a relatively short duration of 24 hours (h) in comparison to conventional testing methods such as bacterial culture that require several days;

high throughput: compared with the common first-generation sequencing and quantitative PCR detecting methods, the present disclosure identifies the presence of all bacteria in the sample in a single experiment;

simple interpretation: in contrast to, for example, second-generation sequencing, the present disclosure offers very simple interpretation, as the presence of the strain in the sample can be immediately confirmed by the two-dimensional position of the probe in the scanning map of the microarray, requiring no complex data analysis process;

specificity: comparing with recent developments such as macro-genome sequencing, the present disclosure is highly targeted, with specific primers amplifying only the target genes of the target species without generating a large amount of useless data, and even if there is non-specific amplification of primers, it can be excluded by specific probes in subsequent hybridization experiments, without interfering with the final results; and expansibility: the factors that limit the number of strains that can be detected in a single experiment are the number of probes that can be accommodated on a single microarray and the adequacy of the specificity of the known gene sequences or partial sequences of the strains to be tested, with these two conditions being met, the present disclosure is scalable to detect more species of bacteria present in the sample if required.

DETAILED DESCRIPTION OF THE EMBODIMENTS

Figure 1:
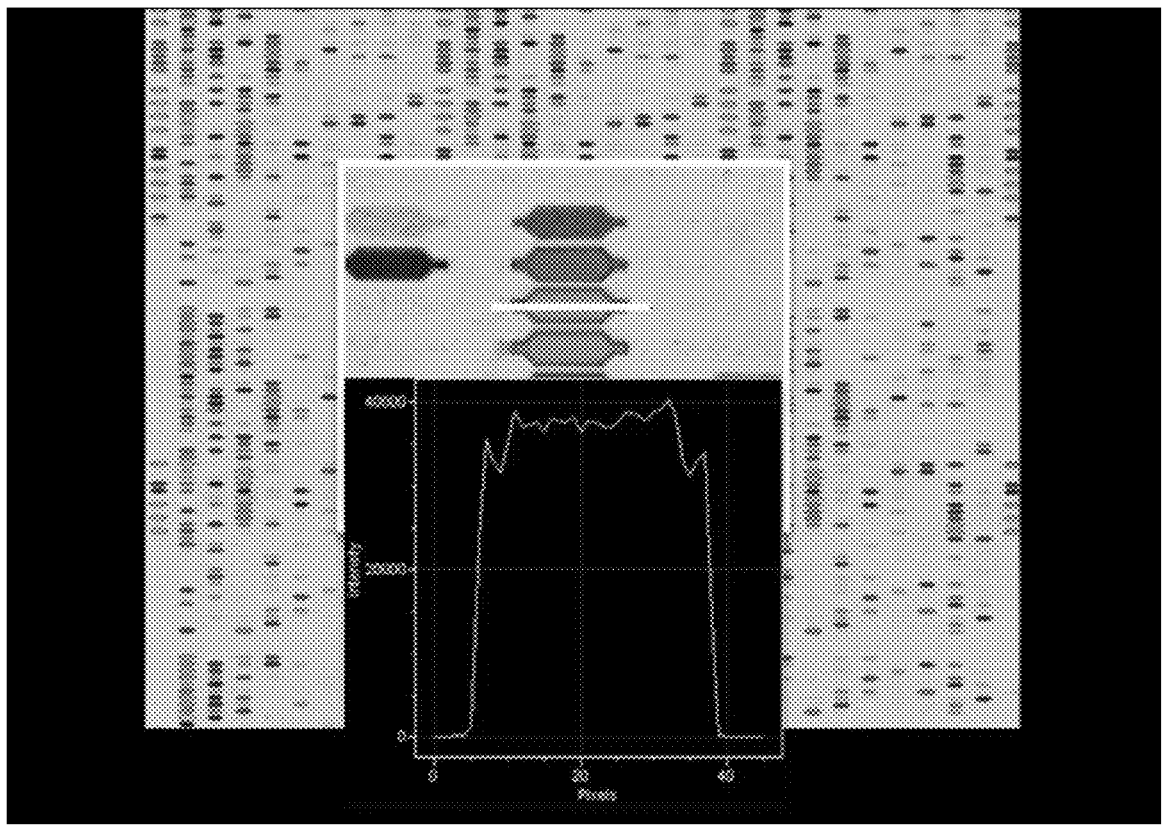
FIG. 1 shows a schematic diagram of the hybridization signal after microarray scanning of the present disclosure and the determination of the fluorescence optical imaging (FOI) value.

The disclosure provides probes for rapid detection of clinical ophthalmic microorganisms, and the probes includes probes for detecting *Staphylococcus epidermidis*, probes for detecting *Staphylococcus aureus*, probes for detecting *Staphylococcus haemolyticus*, probes for detecting *Pseudomonas aeruginosa*, probes for detecting *Staphylococcus hominis*, probes for detecting *Serratia marcescens*, probes for detecting *Escherichia coli*, probes for detecting *Bacillus subtilis* and probes for detecting *Enterobacter cloacae*, with sequences as shown in Table 1.

TABLE 1

| Sequence Table of Probes | | |
|---|---|---|
| Strain | Sequence | S/N |
| Staphylococcus epidermidis | ATCAAACGACTAATACAATTACTGG | SEQ ID NO. 1 |
| | ACTAATACAATTACTGGCACGCCAA | SEQ ID NO. 2 |
| | AATTACTGGCACGCCAAGTGAAGTA | SEQ ID NO. 3 |
| | GCACGCCAAGTGAAGTAGGAACTAC | SEQ ID NO. 4 |
| | AGTGAAGTAGGAACTACAACTGTGA | SEQ ID NO. 5 |
| | AGGAACTACAACTGTGACAGTTAAT | SEQ ID NO. 6 |
| | CAACTGTGACAGTTAATACGACTGA | SEQ ID NO. 7 |
| | ACAGTTAATACGACTGATGCTACTG | SEQ ID NO. 8 |
| | TACGACTGATGCTACTGGGAACGTA | SEQ ID NO. 9 |
| | ATGCTACTGGGAACGTAACATCTAA | SEQ ID NO. 10 |
| | GGGAACGTAACATCTAAGCAATTTA | SEQ ID NO. 11 |
| | AACATCTAAGCAATTTACAATAACG | SEQ ID NO. 12 |
| | ATACAATCAGCCCTGTTGTAAATGT | SEQ ID NO. 13 |
| | AGCCCTGTTGTAAATGTGACGCCAA | SEQ ID NO. 14 |
| | TGTAAATGTGACGCCAAGTCAAGCA | SEQ ID NO. 15 |
| | TGACGCCAAGTCAAGCATCAGAAGT | SEQ ID NO. 16 |
| | AGTCAAGCATCAGAAGTTTTCACGC | SEQ ID NO. 17 |
| | ATCAGAAGTTTTCACGCCGATTAAT | SEQ ID NO. 18 |
| | TTTTCACGCCGATTAATCCAATTAC | SEQ ID NO. 19 |
| | CCGATTAATCCAATTACGATAACTG | SEQ ID NO. 20 |
| Staphylococcus aureus | ACATGTGTTACCTGTACAAACGAAT | SEQ ID NO. 21 |
| | TGTACAAACGAATAAAATCTTCATA | SEQ ID NO. 22 |
| | TAAAATCTTCATAGTTCACATCCTT | SEQ ID NO. 23 |
| | AGTTCACATCCTTTAATAATGTGAT | SEQ ID NO. 24 |
| | TTAATAATGTGATTACCTGCAGCTT | SEQ ID NO. 25 |
| | TTACCTGCAGCTTTTAACATGCGAT | SEQ ID NO. 26 |
| | TTTAACATGCGATTCATAATTGCTT | SEQ ID NO. 27 |
| | TTCATAATTGCTTCTGTATTATCAT | SEQ ID NO. 28 |
| | TCTGTATTATCATTCAGCTCAAAGC | SEQ ID NO. 29 |
| | TTCAGCTCAAAGCCGTATATATACG | SEQ ID NO. 30 |
| | CCGTATATATACGCCGCTGAAATAT | SEQ ID NO. 31 |
| | GCCGCTGAAATATTTTCATTTTCAT | SEQ ID NO. 32 |
| | TTTTCATTTTCATCAAGTGAATGTA | SEQ ID NO. 33 |
| | TCAAGTGAATGTAACACATCATAAA | SEQ ID NO. 34 |
| | AACACATCATAAAGATTATGACTTG | SEQ ID NO. 35 |
| | AGATTATGACTTGCTTGTTTAACAT | SEQ ID NO. 36 |
| | GCTTGTTTAACATCATTGTCATCCT | SEQ ID NO. 37 |
| | TCATTGTCATCCTGACATAATTGAA | SEQ ID NO. 38 |
| | TGACATAATTGAATGAATTGCGCTT | SEQ ID NO. 39 |
| | ATGAATTGCGCTTCACTTGGTATAA | SEQ ID NO. 40 |
| Staphylococcus haemolyticus | GGATGCTAGACAGTTAGCATGTATT | SEQ ID NO. 41 |
| | ACAGTTAGCATGTATTGTCAGAGAA | SEQ ID NO. 42 |
| | ATGTATTGTCAGAGAAACACCTTAT | SEQ ID NO. 43 |
| | CAGAGAAACACCTTATATTGCAAAC | SEQ ID NO. 44 |
| | ACCTTATATTGCAAACAATGGGGTG | SEQ ID NO. 45 |
| | TGCAAACAATGGGGTGACTATTGTT | SEQ ID NO. 46 |
| | TGGGGTGACTATTGTTACTGGTGCA | SEQ ID NO. 47 |
| | TATTGTTACTGGTGCATTGGTTAAT | SEQ ID NO. 48 |
| | TGGTGCATTGGTTAATCCTAATCCA | SEQ ID NO. 49 |
| | GGTTAATCCTAATCCAATTGATCGA | SEQ ID NO. 50 |
| | TAATCCAATTGATCGACATATTACA | SEQ ID NO. 51 |
| | TGATCGACATATTACAGTTGATAGT | SEQ ID NO. 52 |
| | TATTACAGTTGATAGTTATATCGAA | SEQ ID NO. 53 |
| | TGATAGTTATATCGAATGGGTTAAT | SEQ ID NO. 54 |
| | TATCGAATGGGTTAATGGTGAGTTA | SEQ ID NO. 55 |
| | GGTTAATGGTGAGTTAAATAATAGA | SEQ ID NO. 56 |
| | TGAGTTAAATAATAGAGGTATATTA | SEQ ID NO. 57 |
| | TAATAGAGGTATATTAACCTTTATT | SEQ ID NO. 58 |
| | TATATTAACCTTTATTCAAAATTAT | SEQ ID NO. 59 |
| | CTTTATTCAAAATTATAGTCGACAA | SEQ ID NO. 60 |
| Pseudomonas aeruginosa | GATCAACACCACCCTGGCGGTGATG | SEQ ID NO. 61 |
| | CACCCTGGCGGTGATGTTCGGCTCG | SEQ ID NO. 62 |
| | GGTGATGTTCGGCTCGGACTACATC | SEQ ID NO. 63 |
| | CGGCTCGGACTACATCGGCGACTTC | SEQ ID NO. 64 |
| | CTACATCGGCGACTTCATGCACGGC | SEQ ID NO. 65 |
| | CGACTTCATGCACGGCAGCCAGGTG | SEQ ID NO. 66 |
| | GCACGGCAGCCAGGTGCGCAAGGTG | SEQ ID NO. 67 |
| | CCAGGTGCGCAAGGTGGTGGTCCAG | SEQ ID NO. 68 |
| | CAAGGTGGTGGTCCAGGCCGACGGC | SEQ ID NO. 69 |
| | GGTCCAGGCCGACGGCGCCAAGCGC | SEQ ID NO. 70 |
| | CGACGGCGCCAAGCGCCTGGGCATC | SEQ ID NO. 71 |
| | CAAGCGCCTGGGCATCGACGACATC | SEQ ID NO. 72 |
| | GGGCATCGACGACATCGGCCGGCTT | SEQ ID NO. 73 |

TABLE 1-continued

Sequence Table of Probes

| Strain | Sequence | S/N |
|---|---|---|
| | CGACATCGGCCGGCTTCACGTGCGC | SEQ ID NO. 74 |
| | CCGGCTTCACGTGCGCAACGAGCAG | SEQ ID NO. 75 |
| | CGTGCGCAACGAGCAGGGCGAGATG | SEQ ID NO. 76 |
| | CGAGCAGGGCGAGATGGTGCCGCTG | SEQ ID NO. 77 |
| | CGAGATGGTGCCGCTGGCGACGTTC | SEQ ID NO. 78 |
| | GCCGCTGGCGACGTTCGCCAAGGCC | SEQ ID NO. 79 |
| | GACGTTCGCCAAGGCCGCCTGGACC | SEQ ID NO. 80 |
| Staphylococcus hominis | TACTATGTCGCAAGTGAAACAATTG | SEQ ID NO. 81 |
| | GCAAGTGAAACAATTGAGGTTAAAG | SEQ ID NO. 82 |
| | ACAATTGAGGTTAAAGACCTTATAG | SEQ ID NO. 83 |
| | GTTAAAGACCTTATAGATTTCTTAC | SEQ ID NO. 84 |
| | CTTATAGATTTCTTACAAGAACATT | SEQ ID NO. 85 |
| | TTCTTACAAGAACATTTAGCAAAAT | SEQ ID NO. 86 |
| | GAACATTTAGCAAAATATAAAGTTC | SEQ ID NO. 87 |
| | GCAAAATATAAAGTTCCTAAGATAT | SEQ ID NO. 88 |
| | AAAGTTCCTAAGATATATCAACGCG | SEQ ID NO. 89 |
| | AAGATATATCAACGCGTCAATGCAT | SEQ ID NO. 90 |
| | CAACGCGTCAATGCATTACCTTATA | SEQ ID NO. 91 |
| | AATGCATTACCTTATACTTCTACTG | SEQ ID NO. 92 |
| | CCTTATACTTCTACTGGAAAATTAC | SEQ ID NO. 93 |
| | TCTACTGGAAAATTACAACGTAATA | SEQ ID NO. 94 |
| | AAATTACAACGTAATAAAGTTGGAA | SEQ ID NO. 95 |
| | CGTAATAAAGTTGGAACTGAGGATC | SEQ ID NO. 96 |
| | GTTGGAACTGAGGATCATTAAATGA | SEQ ID NO. 97 |
| | GAGGATCATTAAATGAAAATTATTG | SEQ ID NO. 98 |
| | TAAATGAAAATTATTGATATACAAT | SEQ ID NO. 99 |
| | ATTATTGATATACAATTTTATTACT | SEQ ID NO. 100 |
| Serratia marcescens | GTTGTTCGCCAGAGTCAAGCTGGAA | SEQ ID NO. 101 |
| | CGCCAGAGTCAAGCTGGAAACCGGC | SEQ ID NO. 102 |
| | AGTCAAGCTGGAAACCGGCGCGCCG | SEQ ID NO. 103 |
| | GCTGGAAACCGGCGCGCCGCAGGCC | SEQ ID NO. 104 |
| | CGACCAATCGATTGGCACCGATCAA | SEQ ID NO. 105 |
| | ATCGATTGGCACCGATCAAAACCGG | SEQ ID NO. 106 |
| | TGGCACCGATCAAAACCGGCGCTAT | SEQ ID NO. 107 |
| | CGATCAAAACCGGCGCTATGTCCTG | SEQ ID NO. 108 |
| | AAACCGGCGCTATGTCCTGGTCGTC | SEQ ID NO. 109 |
| | GCGCTATGTCCTGGTCGTCGATGAG | SEQ ID NO. 110 |
| | TGTCCTGGTCGTCGATGAGAATGAC | SEQ ID NO. 111 |
| | GAATGACAAAACCGAATACCGCCCC | SEQ ID NO. 112 |
| | CAAAACCGAATACCGCCCCGTTGAA | SEQ ID NO. 113 |
| | CGAATACCGCCCCGTTGAACTTGGC | SEQ ID NO. 114 |
| | CCGCCCCGTTGAACTTGGCCCGGTC | SEQ ID NO. 115 |
| | CGTTGAACTTGGCCCGGTCGTTGAA | SEQ ID NO. 116 |
| | ACTTGGCCCGGTCGTTGAAGGACTG | SEQ ID NO. 117 |
| | CCCGGTCGTTGAAGGACTGCGCGTG | SEQ ID NO. 118 |
| | CGTTGAAGGACTGCGCGTGATAGAG | SEQ ID NO. 119 |
| | AGGACTGCGCGTGATAGAGCACGGC | SEQ ID NO. 120 |
| Escherichia coli | TGAACTTGCCTTTGCCGCCGGGATC | SEQ ID NO. 121 |
| | CTTTGCCGCCGGGATCACGCCGGTT | SEQ ID NO. 122 |
| | CGGGATCACGCCGGTTGGGGTCAGC | SEQ ID NO. 123 |
| | GCCGGTTGGGGTCAGCAGCTATTCC | SEQ ID NO. 124 |
| | GGTCAGCAGCTATTCCGACTATCCT | SEQ ID NO. 125 |
| | CTATTCCGACTATCCTCCACAAGCG | SEQ ID NO. 126 |
| | CTATCCTCCACAAGCGCAAAAGATT | SEQ ID NO. 127 |
| | ACAAGCGCAAAAGATTGAGCAGGTT | SEQ ID NO. 128 |
| | AAAGATTGAGCAGGTTTCCACCTGG | SEQ ID NO. 129 |
| | GCAGGTTTCCACCTGGCAGGGGATG | SEQ ID NO. 130 |
| | CACCTGGCAGGGGATGAATCTGGAA | SEQ ID NO. 131 |
| | GGGGATGAATCTGGAACGCATTGTC | SEQ ID NO. 132 |
| | TCTGGAACGCATTGTCGCGCTGAAA | SEQ ID NO. 133 |
| | CATTGTCGCGCTGAAACCCGATCTG | SEQ ID NO. 134 |
| | GCTGAAACCCGATCTGGTGATTGCC | SEQ ID NO. 135 |
| | CGATCTGGTGATTGCCTGGCGTGGA | SEQ ID NO. 136 |
| | GATTGCCTGGCGTGGAGGTAATGCC | SEQ ID NO. 137 |
| | GCGTGGAGGTAATGCCGAGCGGCAG | SEQ ID NO. 138 |
| | TAATGCCGAGCGGCAGGTTGACCAG | SEQ ID NO. 139 |
| | GCGGCAGGTTGACCAGCTGGCTTCG | SEQ ID NO. 140 |
| Bacillus subtilis | CGGAGGTTCTGCTGACCTAGCGGGA | SEQ ID NO. 141 |
| | AGGTTCTGCTGACCTAGCGGGATCG | SEQ ID NO. 142 |
| | TTCTGCTGACCTAGCGGGATCGAAC | SEQ ID NO. 143 |
| | TGCTGACCTAGCGGGATCGAACAAA | SEQ ID NO. 144 |
| | TGACCTAGCGGGATCGAACAAAACG | SEQ ID NO. 145 |

TABLE 1-continued

Sequence Table of Probes

| Strain | Sequence | S/N |
|---|---|---|
| | CCTAGCGGGATCGAACAAAACGACT | SEQ ID NO. 146 |
| | AGCGGGATCGAACAAAACGACTATT | SEQ ID NO. 147 |
| Enterobacter cloacae | GTCAGTAATGACGCACCTGAATATA | SEQ ID NO. 148 |
| | AGTAATGACGCACCTGAATATATTC | SEQ ID NO. 149 |
| | CGCGTAGGATCATATTTAACCAGCG | SEQ ID NO. 150 |
| | GTAGGATCATATTTAACCAGCGATT | SEQ ID NO. 151 |
| | GGATCATATTTAACCAGCGATTATG | SEQ ID NO. 152 |
| | TCATATTTAACCAGCGATTATGGAC | SEQ ID NO. 153 |
| | TATTTAACCAGCGATTATGGACGCG | SEQ ID NO. 154 |
| | TTAACCAGCGATTATGGACGCGTTG | SEQ ID NO. 155 |
| | ACCAGCGATTATGGACGCGTTGATT | SEQ ID NO. 156 |

The probes for detecting *Staphylococcus epidermidis* include probes with nucleotide sequences as shown in SEQ ID NO.1-20 respectively;

The probes for detecting *Staphylococcus aureus* include probes with nucleotide sequences as shown in SEQ ID NO.21-40 respectively;

The probes for detecting *Staphylococcus haemolyticus* include probes with nucleotide sequences as shown in SEQ ID NO.41-60 respectively;

The probes for detecting *Pseudomonas aeruginosa* include probes with nucleotide sequences as shown in SEQ ID NO.61-80 respectively;

The probes for detecting *Staphylococcus hominis* include probes with nucleotide sequences as shown in SEQ ID NO.81-100 respectively;

The probes for detecting *Serratia marcescens* include probes with nucleotide sequences as shown in SEQ ID NO.101-120 respectively;

The probes for detecting *Escherichia coli* include probes with nucleotide sequences as shown in SEQ ID NO.121-140 respectively;

The probes for detecting *Bacillus subtilis* include probes with nucleotide sequences as shown in SEQ ID NO.141-147 respectively; and The probes for detecting *Enterobacter cloacae* include probes with nucleotide sequences as shown in SEQ ID NO.148-156, respectively.

According to the present disclosure, after collecting strains in clinical culture and performing 16S rDNA sequencing to determine strain information, a genome sequence search of the strains is performed; after finding the conserved sequence of a single strain, the conserved sequences of all strains are then compared two-by-two to find all similar sequences and exclude the same, and the strain-specific conserved gene fragments (gene sequences with >95 percent (%) endogeneity and <75% interspecies homology) are obtained by further comparison with the National Center for Biotechnology Information (NCBI) database for probe design; in the present disclosure, the probe design is conducted on an longest common subsequence (LCS) microarray using Tiling array; Tiling array probes are designed for each of the above strains of polymerase chain reaction (PCR) products, and multiple probe sequences are designed for regions where mutations are present, with a total of 2,117 probes are designed and 555 probes are functional; the probes are hybridized with the fluorescent PCR products of each strain and the probe with the strongest hybridization signal is selected; the signal is then compared with the hybridization signal of other strains to select the probe with the best specificity as the final 86 probes used on the microarray for detecting pathogenic bacteria. The proposed probes show the strongest hybridization signal values and the best specificity against the target strains, and produce no signal or a signal value close to the background signal against non-target strains.

The disclosure also provides a microarray for rapid detection of clinical ophthalmic microorganisms, and the microarray contains the probes described in the technical schemes of the present disclosure; the microarray adopts the method of hybridization, which preferably includes the following steps: the fluorescent PCR product is purified using LCS_beads magnetic beads, excess primers and impurities are removed, and the fluorescence optical imaging (FOI) is determined by measuring absorbance values at 260 nanometer (nm) and 550 nm using an ASP-3700 micro spectrophotometer, where the hybridization works best when the FOI value is in the range of 20-50.

The disclosure also provides primers for rapid detection of clinical ophthalmic microorganisms, where the primers include primers for detecting *Staphylococcus epidermidis, Staphylococcus aureus, Staphylococcus haemolyticus, Pseudomonas aeruginosa, Staphylococcus hominis, Serratia marcescens, Escherichia coli, Bacillus subtilis* and *Enterobacter cloacae* as shown in Table 2, respectively.

The primers for detecting *Staphylococcus epidermidis* include a forward primer with a nucleotide sequence as shown in SEQ ID NO.157 and a reverse primer with a nucleotide sequence as shown in SEQ ID NO.158;

the primers for detecting *Staphylococcus aureus* include a forward primer with a nucleotide sequence as shown in SEQ ID NO.159 and a reverse primer with a nucleotide sequence as shown in SEQ ID NO.160;

the primers for detecting *Staphylococcus haemolyticus* include a forward primer with a nucleotide sequence as shown in SEQ ID NO.161 and a reverse primer with a nucleotide sequence as shown in SEQ ID NO.162;

the primers for detecting *Pseudomonas aeruginosa* include a forward primer with a nucleotide sequence as shown in SEQ ID NO.163 and a reverse primer with a nucleotide sequence as shown in SEQ ID NO.164;

the primers for detecting *Staphylococcus hominis* include a forward primer with a nucleotide sequence as shown in SEQ ID NO.165 and a reverse primer with a nucleotide sequence as shown in SEQ ID NO.166;

the primers for detecting *Serratia marcescens* include a forward primer with a nucleotide sequence as shown in SEQ ID NO.167 and a reverse primer with a nucleotide sequence as shown in SEQ ID NO.168;

the primers for detecting *Escherichia coli* include a forward primer with a nucleotide sequence as shown in SEQ ID NO.169 and a reverse primer with a nucleotide sequence as shown in SEQ ID NO.170;

the primers for detecting *Bacillus subtilis* include a forward primer with a nucleotide sequence as shown in SEQ ID NO.171 and a reverse primer with a nucleotide sequence as shown in SEQ ID NO.172; and the primers for detecting *Enterobacter cloacae* include a forward primer with a nucleotide sequence as shown in SEQ ID NO.173 and a reverse primer with a nucleotide sequence as shown in SEQ ID No.174.

The probes, microarray, primers and kit for rapid detection of clinical ophthalmic microorganisms according to the present disclosure are further described in detail with reference to the following specific embodiments. The technical scheme of the present disclosure includes but is not limited to the following embodiments.

Embodiment 1

Primer Screening

The specific DNA sequences of strains are screened by whole genome alignment, specifically by downloading all

TABLE 2

Primers for rapid detection of clinical ophthalmic microorganisms

| Strain | F | R |
|---|---|---|
| *Staphylococcus epidermidis* | GGTCTACCTTCAGGGTTATCTTTTT (SEQ ID NO. 157) | AGTCCTTGTGGCAATCCTGTTA (SEQ ID NO. 158) |
| *Staphylococcus aureus* | ACTTTCCGCTAATGGGCTACG (SEQ ID NO. 159) | TGTGCCGAGTAATAAGGTGGC (SEQ ID NO. 160) |
| *Staphylococcus haemolyticus* | ATGTGCGAAAACAAATGACGA (SEQ ID NO. 161) | GCTTCTAAAGCTATGCCATACTCTT (SEQ ID NO. 162) |
| *Pseudomonas aeruginosa* | GGCGTGAGCATGGACGA (SEQ ID NO. 163) | CCGTTGTAGCGGGTCAGTT (SEQ ID NO. 164) |
| *Staphylococcus hominis* | GGGGTCAGATTCCAGCACTT (SEQ ID NO. 165) | TTAGGCGTCGTAATCGGAGA (SEQ ID NO. 166) |
| *Serratia marcescens* | CTGTCACCTGGGTTGTTCGC (SEQ ID NO. 167) | GGGAAAGTCATGTCGCGTCTC (SEQ ID NO. 168) |
| *Escherichia coli* | GCTTTCTCCCGCCAACAC (SEQ ID NO. 169) | CATCGACCCACATCACTTTTATT (SEQ ID NO. 170) |
| *Bacillus subtilis* | CGACAATCGGATTCGGTTCA (SEQ ID NO. 171) | TGTTCGATCCCGCTAGGTCAG (SEQ ID NO. 172) |
| *Enterobacter cloacae* | TCTGGCTAAGGAACGGGTCT (SEQ ID NO. 173) | GCGTCTTGTGAGTGCAGTCTAA (SEQ ID NO. 174) |

According to the present disclosure, after collecting strains in clinical culture and performing 16S rDNA sequencing to determine strain information, a genome sequence search of the strains is performed; after finding the conserved sequence of a single strain, the conserved sequences of all strains are then compared two-by-two to find all similar sequences and exclude the same, and the strain-specific conserved gene fragments (gene sequences with >95 percent (%) endogeneity and <75% interspecies homology) are obtained by further comparison with the NCBI database for probe design; a batch of primers is designed using primer5 and the designed primers are screened using DNAstat to obtain the primer combinations.

In the present disclosure, all 5' ends of the forward primers in the primers are preferably labeled with a fluorescent group, where the fluorescent group preferably includes Cy3; according to the disclosure, a Cy3 fluorescent group is added at the 5' end of the forward primer to obtain a strain-specific fluorescent primer.

The disclosure also provides a primer-probe set for rapid detection of clinical ophthalmic microorganisms, and the set includes the probe described in the technical scheme and the primer described in the technical scheme.

The disclosure also provides a kit for rapidly clinical detection of ophthalmic microorganisms, and the kit includes that microarray and the primer described in the technical scheme of the present disclosure.

genome sequences of 9 pathogenic bacteria in NCBI, and finding gene sequence segments with intra-species homology>95% (most of them can reach more than 97%) and inter-species homology<75% (most of them are less than 70% or almost no homology between species) in the gene sequences of microorganisms to be detected; Table 3 shows the summary of the genes where the sequences of primers selected by each strain are located.

TABLE 3

Summary of genes where the sequences of primers selected by each strain are located

| Strain to be detected | Gene where the spare sequence of the screened primer is located |
|---|---|
| *Staphylococcus epidermidis* | adhesion |
| *Staphylococcus aureus* | ATP-binding cassette domain-containing protein, peptide ABC transporter substrate-binding protein, protein-tyrosine-phosphatase, threonylcarbamoyl-AMP synthase, iron export ABC transporter permease subunit FetB, ATP-binding cassette domain-containing protein, M42 family peptidase |
| *Staphylococcus haemolyticus* | yqjA, thiamine/molybdopterin biosynthesis ThiF/MoeB-like protein, vraA, siderophore synthetase |

TABLE 3-continued

Summary of genes where the sequences of primers
selected by each strain are located

| Strain to be detected | Gene where the spare sequence of the screened primer is located |
|---|---|
| Pseudomonas aeruginosa | oqxB_1_EU370913, fabZ, acyl-[acyl-carrier-protein]-UDP-N-acetylglucosamine O-acyltransferase, lipid-A-disaccharide synthase |
| Staphylococcus hominis | o-succinylbenzoate-CoA ligase, o-succinylbenzoate synthase, cell division protein FtsK, tRNA-binding protein |
| Serratia marcescens | protease, MexE family multidrug efflux RND transporter periplasmic adaptor subunit, MexE family multidrug efflux RND transporter periplasmic adaptor subunit, AcrB/AcrD/AcrF family protein |
| Escherichia coli | csdA, csdE, YqgE/AlgH family protein, ruvX, PilT/PilU family type 4a pilus ATPase, btuF, mtnN |
| Bacillus subtilis | carB, tkt, sufB |
| Enterobacter cloacae | whole genome screening |

Embodiment 2

Primer Design and PCR Verification

At first, primer5 is used to design individual primers for the selected DNA segments of each strain, and a batch of primers are screened out; at the end, primer selection is carried out on the screened primers with DNAstat software to find out a more suitable primer combination; a primer is synthesized, and a fluorescent group (Cy3) is added to the 5' end of the forward primer, so that the PCR product is fluorescent, and then it can be used to hybridize the microarray of the present disclosure and scanned by a scanner, so that whether the probe is successfully hybridized or not can be identified.

The primers screened and verified in Embodiment 2 (as shown in Table 2) have high specificity and can produce readable fluorescence signals after hybridization.

Embodiment 3

Probe Design and Screening

The number of probes that can be accommodated in one LCS microarray is 3,968 (31*128). In order to screen the probes in the largest range, the disclosure designs the Tiling array probes for the PCR products of various bacteria, i.e. using the isometric displacement method, a certain length of sequence (the selected length in the disclosure is 25 base pair (bp)) is selected from end to end according to the target sequence to form a probe combination, where adjacent probe sequences differ by one base until the entire target is covered. Based on the results of NCBI blast of the PCR product sequences, multiple probes are designed based on the mutated bases, and if a probe covers too many mutations (more than 3 mutations in 25 bp), the probe is discarded. Probes are screened for suitability for hybridization by performing hybridization experiments and selecting products that successfully amplify with fluorescence for hybridization reactions with the microarray. After scanning the microarray, the data is extracted, and analysis of the data is carried out to select probes with good hybridization signals and good specificity.

Embodiment 4

Purification of PCR Products and Calculation of Fluorescence Penetration Density The fluorescing products obtained by amplification using the primers screened in Embodiment 2 are subjected to hybridization reactions with the probes screened in Embodiment 3, and the data are extracted after scanning the microarray. These probes are analyzed for signal on other strain hybridization microarrays, and those with the best specificity (i.e. weaker signal values on other strain hybridization microarrays, close to negative control probes) are selected as the final testing probes for the pathogenic bacteria detection microarrays, as shown in Table 1, with 146 probes in total.

The fluorescent PCR products are purified by LCS_beads magnetic beads, and after removing the excess primers and impurities, the absorbance values at 260 nm and 550 nm are measured by ASP-3700 spectrophotometer to determine the FOI, where FOI at 20-50 is most suitable for hybridization.

Calculation of FOI:

FOI=fluorescence infiltration pmol×(324.5/cDNA nmol) where the amount of Cy3 or Cy5 in the sample (pmol)= $(A/E) \times (1/W) \times (Z) \times df \times 10^6$;

A=the absorbance value of Cy3 at 550 nm or Cy5 at 650 nm;

E=extinction coefficient: Cy3=150,000, Cy5=250,000;

Z=microliters of sample volume;

W=light path=0.1 centimeter (cm);

df=dilution multiple.

In this experiment: FOI=(absorbance value of Cy3 at 550 nm/150,000)×10×10$^6$×((324.5/(absorbance value of Cy3 at 260 nm×50)))

TABLE 4

Fluorescent penetration density in fluorescent PCR products

| PCR products | A550 | A260 | FOI |
|---|---|---|---|
| Staphylococcus haemolyticus | 0.009 | 0.192 | 20.28125 |
| Enterobacter cloacae | 0.01 | 0.313 | 13.82322 |
| Staphylococcus epidermidis | 0.024 | 0.187 | 55.52941 |
| Staphylococcus aureus | 0.015 | 0.205 | 31.65854 |
| Staphylococcus hominis | 0.02 | 0.323 | 26.79051 |
| Pseudomonas aeruginosa | 0.012 | 0.241 | 21.54357 |
| Escherichia coli | 0.02 | 0.265 | 32.65409 |
| Sertia marcescens | 0.011 | 0.247 | 19.26856 |
| Bacillus subtilis | 0.011 | 0.335 | 14.20697 |

According to Table 4, it can be seen that the primers and probes designed by the present disclosure meet the hybridization criteria, and are viable and can be promoted to be made in kind.

Embodiment 5

Microarray hybridization and scanning
Microarray hybridization process
A. System Cleaning Connecting the pathway, replacing the waste microarrays, and cleaning the system with the following solution:

1 milliliter (mL) of 1% Sodium dodecyl sulfate (SDS) preheated at 95 degree Celsius (° C.), where the cleaning is carried out circularly at the highest speed for 20 minutes (min);

carrying out washing with 3 mL nuclease-free water after draining the 1% SDS in the waste tube;

carrying out washing with 1 mL of nuclease-free water preheated at 95° C., and circularly washing at the highest speed for 5-6 min; and carrying out washing with 3 mL nuclease-free water after discarding the nuclease-free water in the waste pipe.

B. Microarray Cleaning

Replacing the microarray with a new one, cleaning it with 1 mL stripping buffer (desorption buffer SP) for 20 min at the bonding speed (pay attention to changing the feeding direction to eliminate bubbles in the microarray);

where the stripping buffer includes: 0.3 Millimolar (mM) ethylene diamine tetraacetic acid (EDTA), 50% formamide, pH 6.6-6.8; such a buffer can clean the nucleic acid sequence that has been hybridized to the probe; and scanning the cleaned microarray with a scanner;

note: the temperature of microarray pedestal is 40° C. during the above system cleaning and microarray cleaning.

This is a step to wash away any impurities that may be present on the microarray and any nucleic acid sequences that may hybridize on it, so as to achieve a relatively clean and homogeneous background ready for hybridization.

C. Sample Hybridization (1) using 1 mL Hybridization buffer (HB) for circular washing for 10 min at the binding speed (500 microliter (μL)/min), where the HB consists of 6×SSPE and 25% Formamide with pH in a range of 6.6-6.8; HB provides a suitable pH environment and salt ion concentration for hybridization reaction, with formamide can reduce the Tm value of DNA double-stranded, so that the sample can be hybridized at 30° C.;

(2) using 1 mL of blocking buffer (BSA) to circularly washing for 5-6 min at the binding speed; where the BSA includes 148 liter (L) of HB and 2 L of 100× heat-treated BSA; the BSA in this buffer can block the probe-free part of the microarray to reduce the background signal of the microarray;

(3) preparation of hybridization sample:

placing 200 nanogram (ng) of purified PCR product+ equal volume of HB with a final volume of 50 μL after denaturation at 95° C. for 5 min quickly put on ice for 3 min, adding the prepared sample into the blocking buffer, mixing well, and then circulating at the binding speed for 16 hours for hybridization.

The hybridization duration is set at 16 hours (h) to make the hybridization reaction long enough to reach the reaction balance, which can be appropriately adjusted in actual operation.

Note: the temperature of microarray pedestal is 40° C. during sample hybridization.

D. Cleaning after Hybridization (1) using 1 mL HB for circularly washing for 20 min at the cleaning speed (100 μL/min) (the temperature of the microarray pedestal is 32° C.);

(2) using 1 mL wash buffer (WB) for washing circularly at 40° C. for 20 min at the cleaning speed, where the WB includes 500 L HB, 500 L nuclear-free water, 20 L 10% SDS. It should be noted that WB should be ready for use.

E. Microarray Scanning

The microarray is scanned according to the GenePix 4000B instructions setting the relevant photomultiplier tube (PMT=300-400), focusing distance (focal position=100-150) and scanning wavelength (532 nm). The hybridization map should be interpreted in conjunction with the information on the position of the probe on the dot matrix. The position of the probe is fixed on the microarray for each strain, and the presence of fluorescence from the probe after hybridization indicates that the sample contains the strain corresponding to the probe at that position.

FIG. 1: schematic diagram of hybridization signal after microarray scanning and determination of FOI value, where the order of hybridization signal intensity is white>red>yellow>green>blue.

Figure 2:
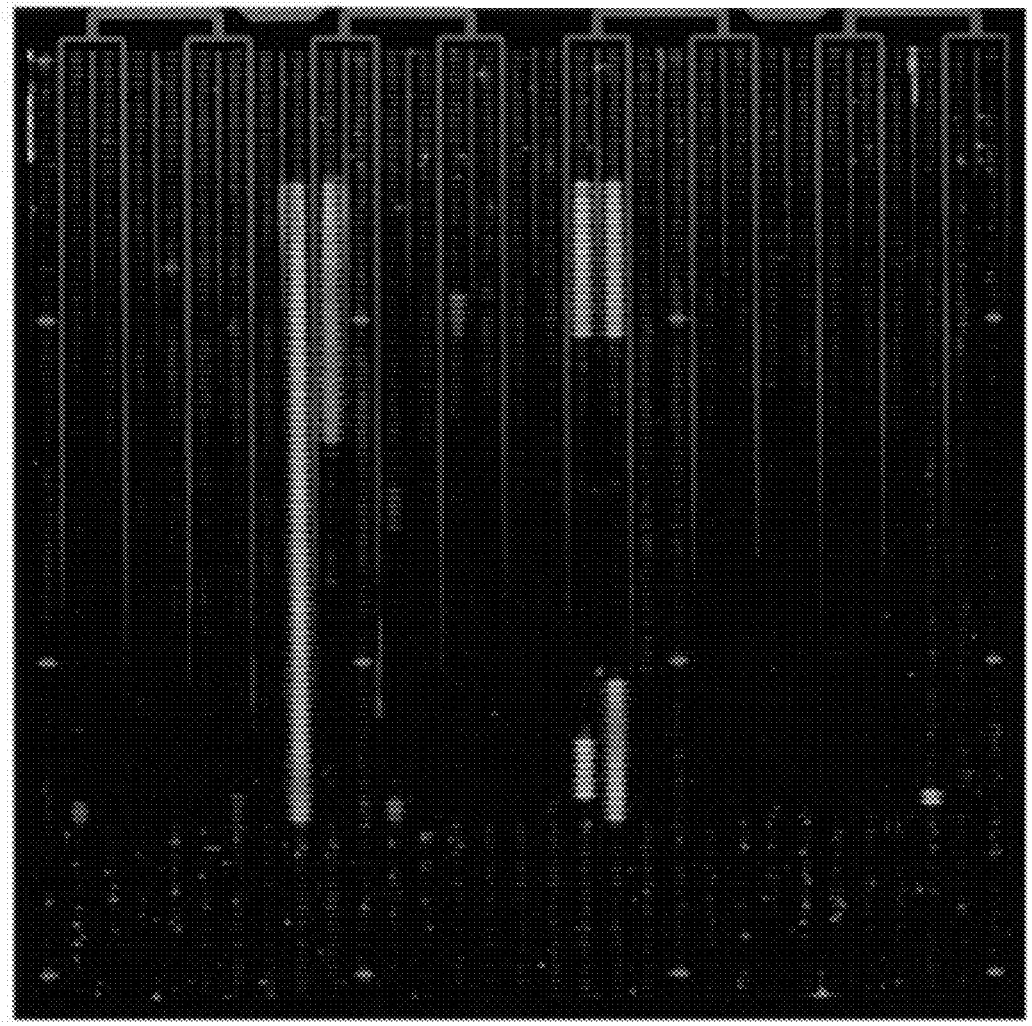
FIG. 2 shows the hybridization signal of detecting *Staphylococcus epidermidis* using the microarray provided by the present disclosure.

FIG. 2: hybridization signal diagram of *Staphylococcus epidermidis*, and it can be seen from the figure that hybridization signal specific to this strain is generated after scanning the microarray, indicating that the microarray can be used to screen and detect *Staphylococcus epidermidis* in clinical practice.

Figure 3:
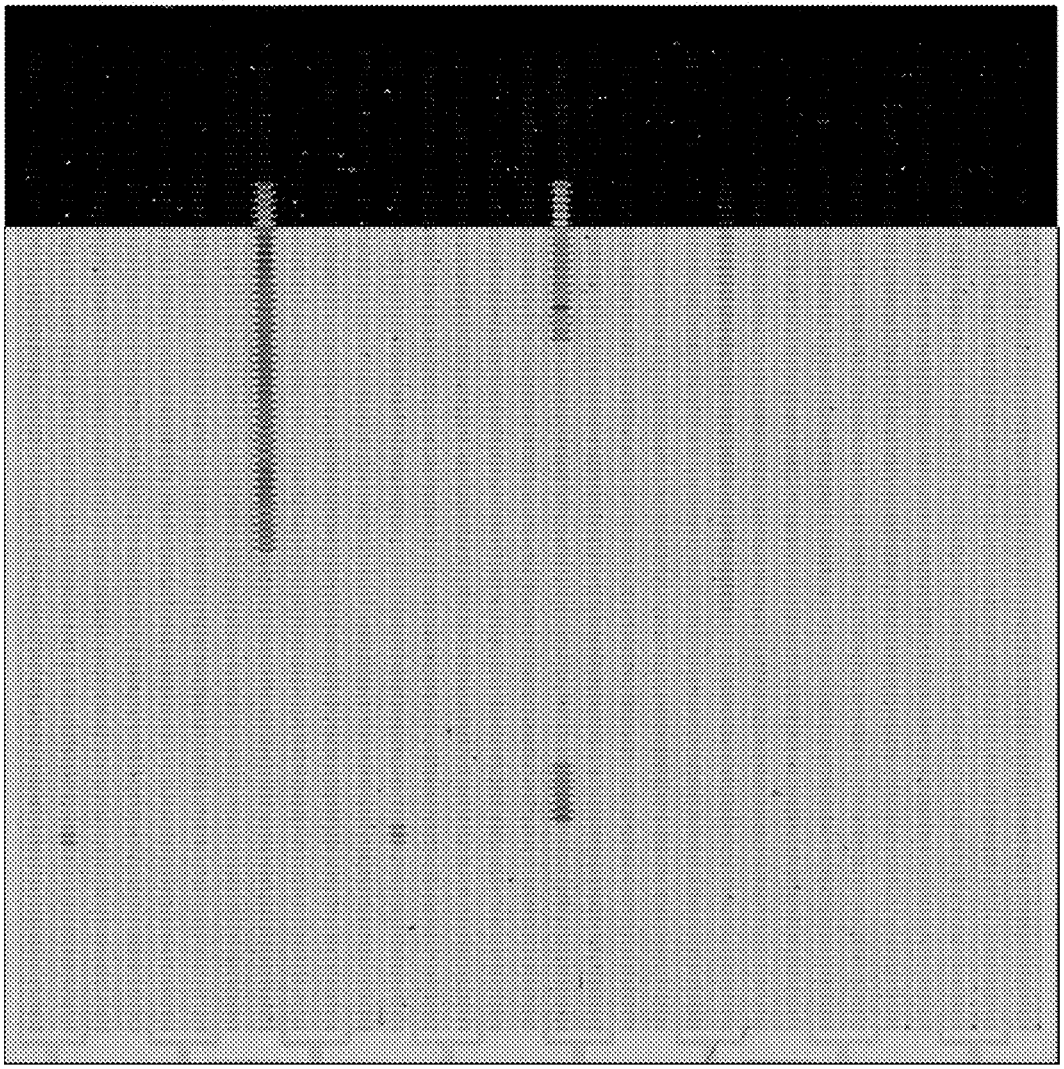
FIG. 3 shows the hybridization signal of detecting *Staphylococcus aureus* using the microarray provided by the present disclosure.

FIG. 3: hybridization signal diagram of *Staphylococcus aureus*, which shows that hybridization signal specific to this strain is generated after scanning the microarray, indicating that the microarray can screen and detect *Staphylococcus aureus* in clinical practice.

Figure 4:
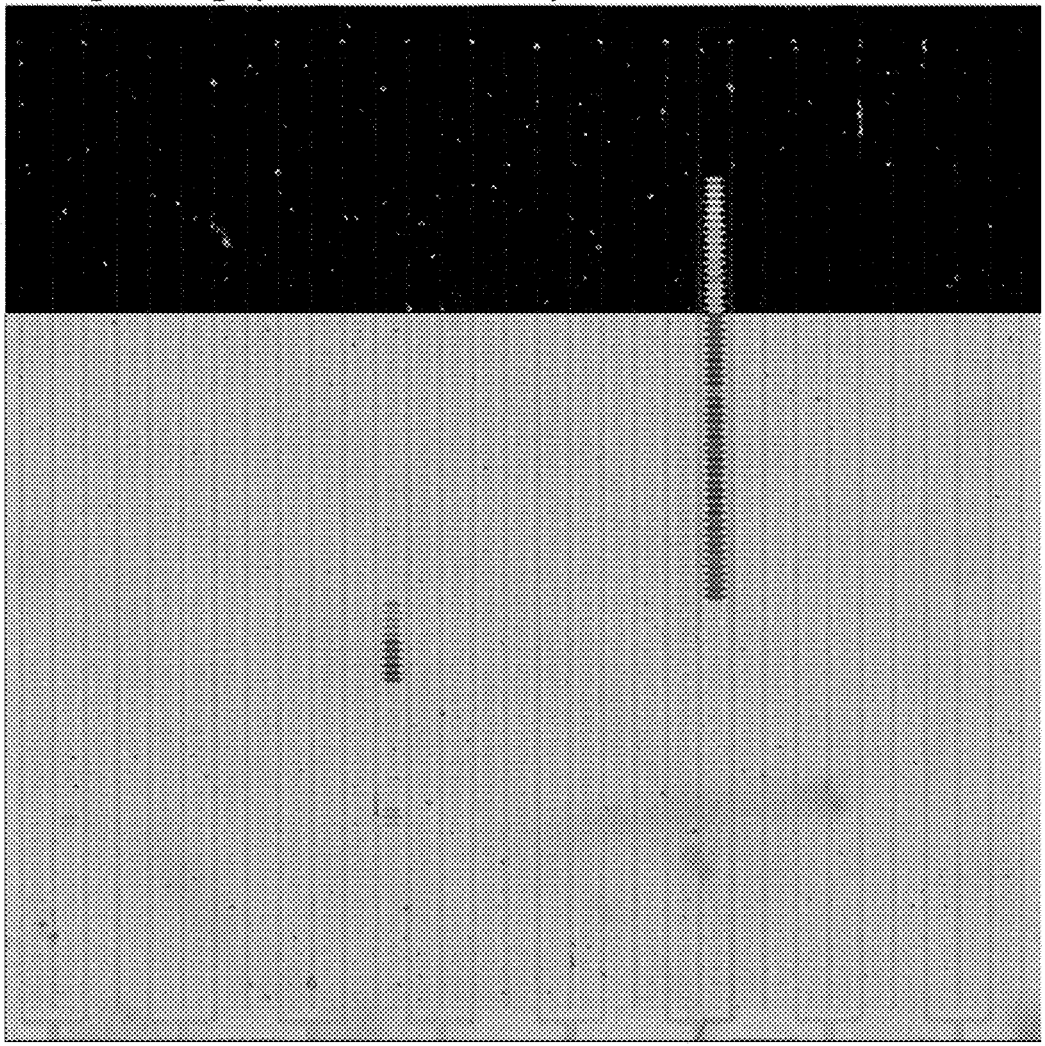
FIG. 4 shows the hybridization signal of detecting *Staphylococcus haemolyticus* using the microarray provided by the present disclosure.

FIG. 4: hybridization signal diagram of *Staphylococcus haemolyticus*, it can be seen that the hybridization signal specific to this strain is generated after scanning the microarray, which indicates that the microarray can screen and detect *Staphylococcus haemolyticus* in clinical practice.

Figure 5:
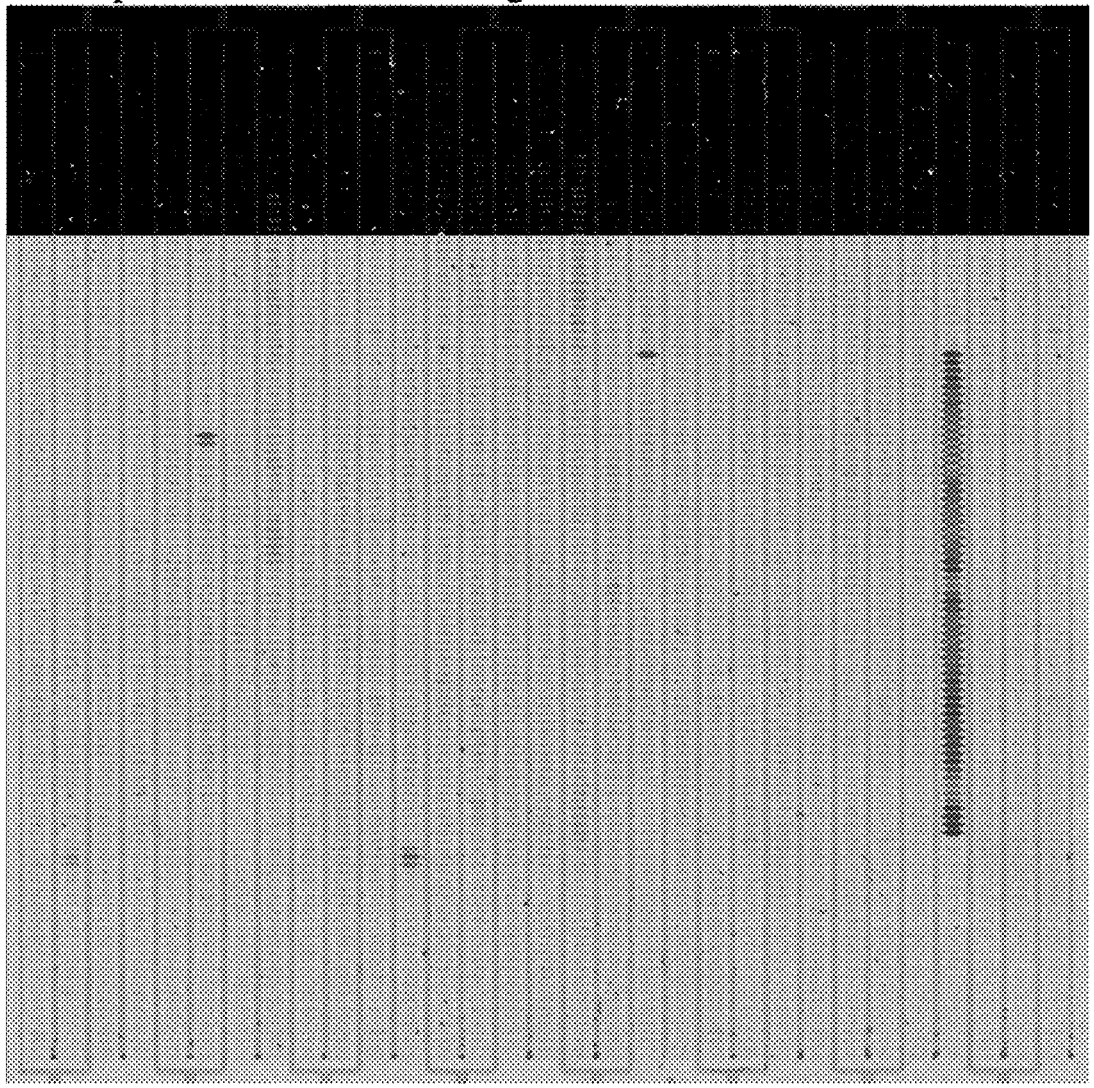
FIG. 5 shows the hybridization signal of detecting *Pseudomonas aeruginosa* using the microarray provided by the present disclosure.

FIG. 5: hybridization signal diagram of *Pseudomonas aeruginosa*, which shows that the hybridization signal specific to this strain is generated after scanning the microarray, indicating that the microarray can screen and detect *Pseudomonas aeruginosa* in clinical practice.

Figure 6:
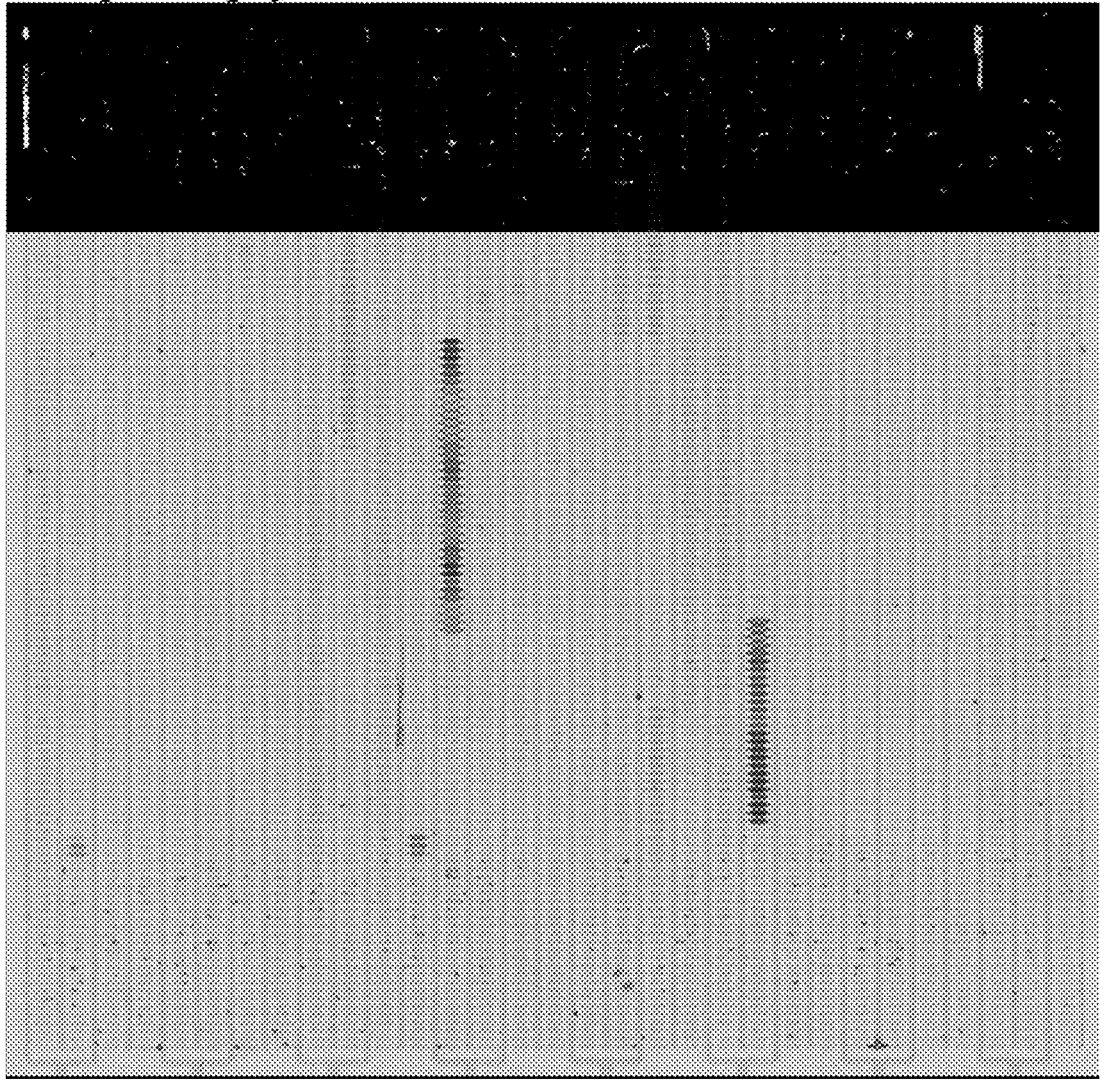
FIG. 6 shows the hybridization signal of detecting *Staphylococcus hominis* using the microarray provided by the present disclosure.

FIG. 6: hybridization signal diagram of *Staphylococcus hominis*. It can be seen from the figure that hybridization signal specific to this strain is generated after scanning the microarray, indicating that the microarray can be used for screening and detecting *Staphylococcus hominis* in clinical practice.

Figure 7:
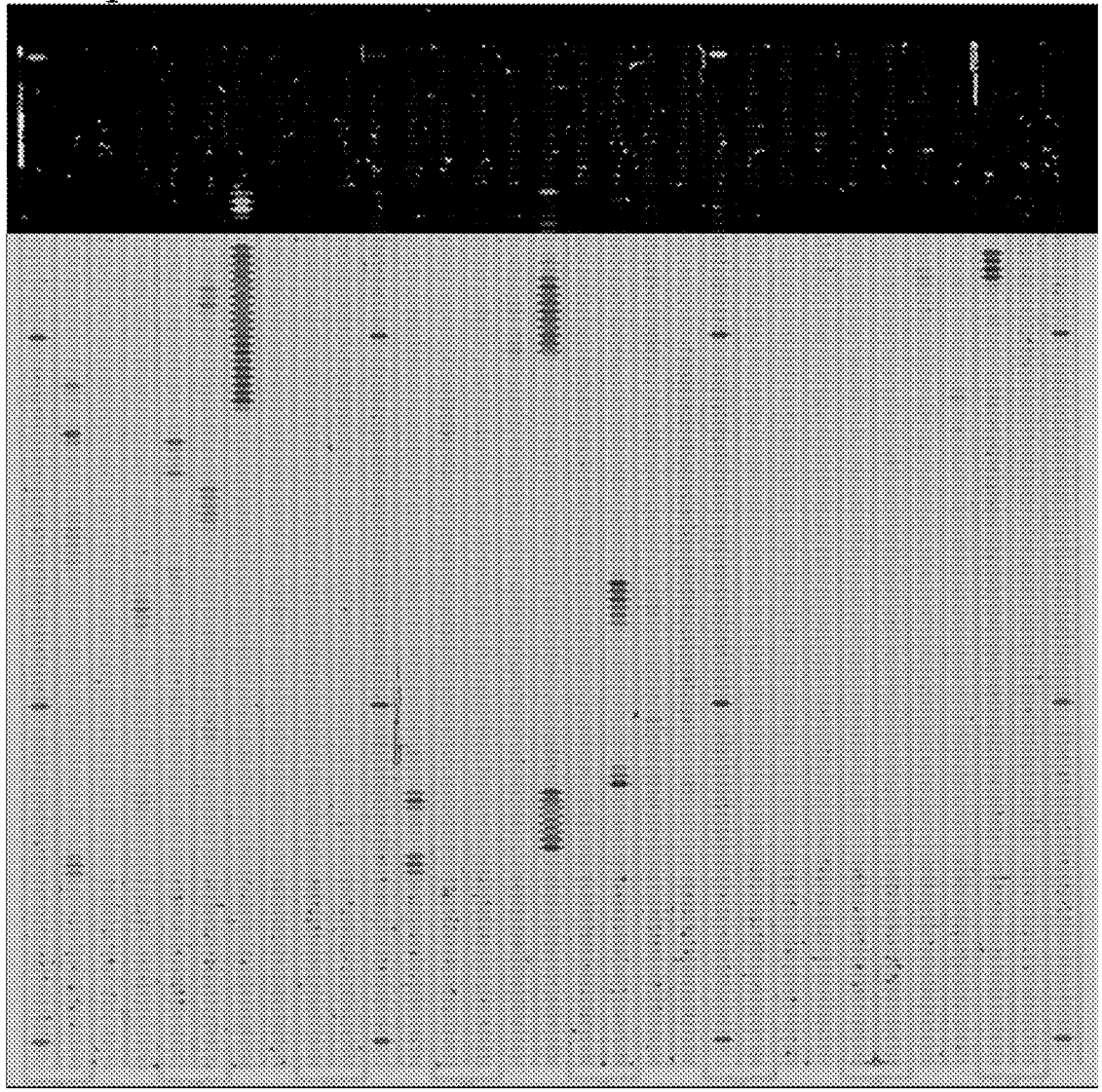
FIG. 7 shows the hybridization signal of detecting *Serratia marcescens* using the microarray provided by the present disclosure.

FIG. 7: hybridization signal diagram of *Serratia marcescens*, which shows that the hybridization signal specific to this strain is generated after scanning the microarray, indicating that the microarray can be used for screening and detecting *Serratia marcescens* in clinical practice.

Figure 8:
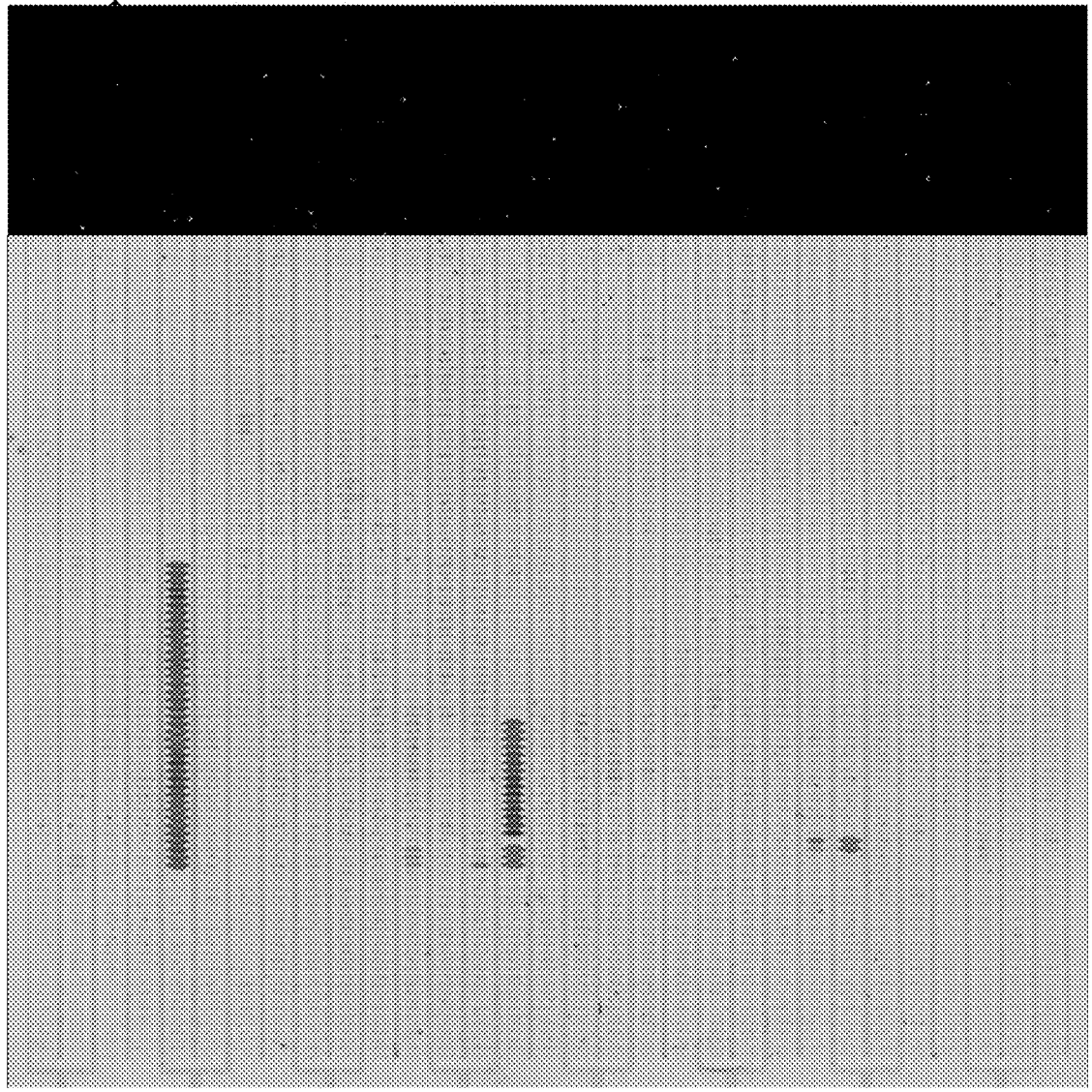
FIG. 8 shows the hybridization signal of detecting *Escherichia coli* using the microarray provided by the present disclosure.

FIG. 8: hybridization signal diagram of *Escherichia coli*, which shows that the hybridization signal specific to this strain is generated after scanning the microarray, indicating that the microarray can screen and detect *Escherichia coli* in clinical practice.

Figure 9:
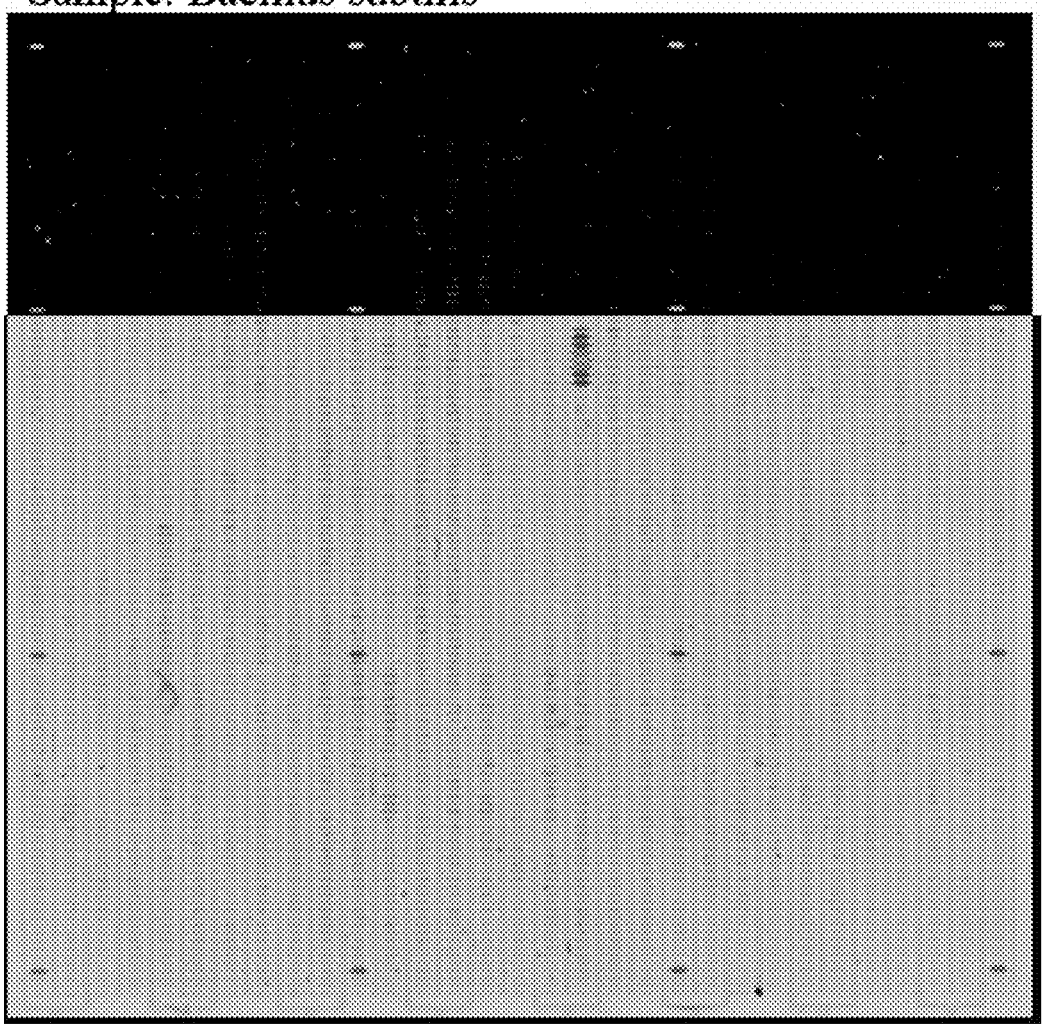
FIG. 9 shows the hybridization signal of detecting *Bacillus subtilis* using the microarray provided by the present disclosure.

FIG. 9: hybridization signal diagram of *Bacillus subtilis*, which shows that the hybridization signal specific to this strain is generated after scanning the microarray, indicating that the microarray can screen and detect *Bacillus subtilis* in clinical application.

Figure 10:
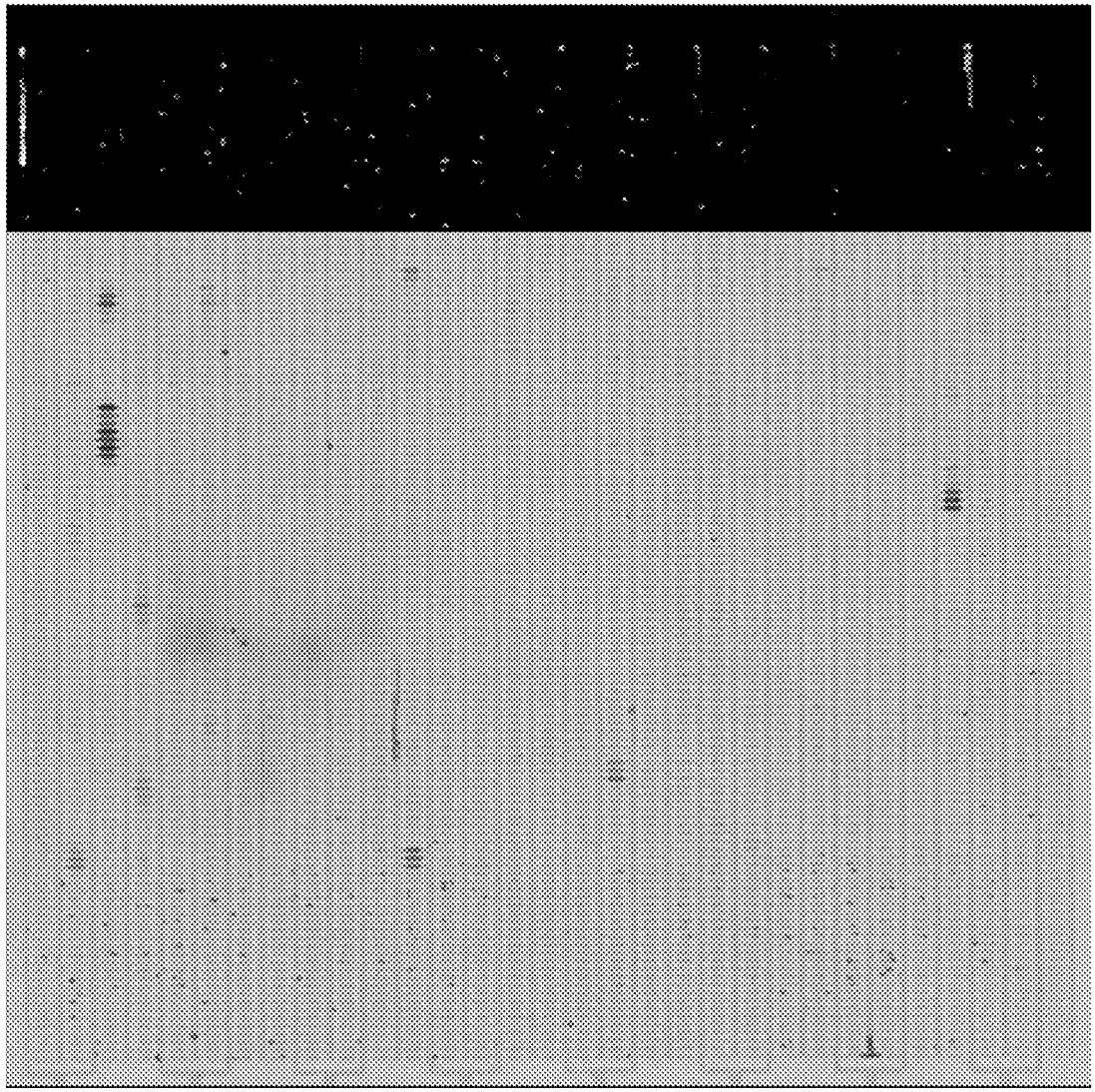
FIG. 10 shows the hybridization signal of detecting *Enterobacter cloacae* using the microarray provided by the present disclosure.

FIG. 10: hybridization signal diagram of *Enterobacter cloacae*, and it can be seen from the figure that the hybridization signal specific to this strain is generated after scanning the microarray, indicating that the microarray can screen and detect *Enterobacter cloacae* in clinical practice.

The above are only the preferred embodiments of the present disclosure, and it should be pointed out that for those of ordinary skill in the technical field, without departing from the principle of the present disclosure, several improvements and embellishments can be made, and these improvements and embellishments should also be regarded as the protection scope of the present disclosure.

What is claimed is:

1. A primer-probe set for rapid detection of clinical ophthalmic microorganisms, comprising probes and primers;
   wherein the probes comprise probes for detecting *Bacillus subtilis*;
   the probes for detecting *Bacillus subtilis* comprise probes with nucleotide sequences as shown in SEQ ID NO.141-147 respectively;
   the primers comprise primers for detecting *Bacillus subtilis*;
   the primers for detecting *Bacillus subtilis* comprise a forward primer with a nucleotide sequence as shown in SEQ ID NO.171 and a reverse primer with a nucleotide sequence as shown in SEQ ID NO.172;
   wherein a 5' end of every forward primer in the primers is labeled with fluorescent group, and the fluorescent group comprises Cyanine 3 (Cy3).

2. A kit for rapid detection of clinical ophthalmic microorganisms, comprising a rapid detection microarray for clinical ophthalmic microorganisms and the primers in the primer-probe set of claim 1, wherein the microarray contains the probes in the primer-probe set of claim 1;
   wherein a 5' end of every forward primer in the primers is labeled with fluorescent group, and the fluorescent group comprises Cy3.

* * * * *